(12) United States Patent
Siciliano et al.

(10) Patent No.: US 12,011,563 B2
(45) Date of Patent: Jun. 18, 2024

(54) DEVICES AND METHODS FOR CONTROLLING NEEDLE RECIPROCATION

(71) Applicant: FK Irons Inc., Doral, FL (US)

(72) Inventors: Gaston Siciliano, Doral, FL (US); Adriano Mendoza, Doral, FL (US)

(73) Assignee: FK Irons Inc., Doral, FL (US)

( * ) Notice: Subject to any disclaimer, the term of this patent is extended or adjusted under 35 U.S.C. 154(b) by 781 days.

(21) Appl. No.: 17/071,851

(22) Filed: Oct. 15, 2020

(65) Prior Publication Data

US 2021/0393936 A1 Dec. 23, 2021

Related U.S. Application Data

(60) Provisional application No. 63/041,402, filed on Jun. 19, 2020.

(51) Int. Cl.
*A61M 37/00* (2006.01)

(52) U.S. Cl.
CPC ..... *A61M 37/0076* (2013.01); *A61M 2205/33* (2013.01); *A61M 2205/52* (2013.01)

(58) Field of Classification Search
CPC .............. A61M 37/00; A61M 37/0076; A61M 2205/52; A61M 2205/33; A61B 17/00491; A61B 17/205
See application file for complete search history.

(56) References Cited

U.S. PATENT DOCUMENTS

| 6,392,460 | B1 | 5/2002 | Vail |
| 6,550,356 | B1 | 4/2003 | Underwood |
| 7,518,479 | B2 | 4/2009 | Mask et al. |
| 8,228,666 | B2 | 7/2012 | Rickard |
| 8,522,647 | B1 | 9/2013 | Dixon |
| 8,685,038 | B2 | 4/2014 | Imran |
| 9,254,376 | B2 | 2/2016 | Colton et al. |
| 9,433,767 | B2 | 9/2016 | Colton et al. |
| 9,452,281 | B2 | 9/2016 | Chan et al. |
| 9,931,185 | B2 | 4/2018 | Gagliano |
| 10,052,469 | B2 | 8/2018 | Chan et al. |

(Continued)

FOREIGN PATENT DOCUMENTS

| AU | 2019359618 | 5/2020 |
| CA | 2923061 | 9/2017 |

(Continued)

OTHER PUBLICATIONS

Patent Cooperation Treaty, "International Preliminary Report on Patentability" issued in International Patent Application No. PCT/US21/37837, dated Dec. 13, 2022; document of 5 pages.

(Continued)

*Primary Examiner* — Vi X Nguyen
(74) *Attorney, Agent, or Firm* — Akerman LLP; Peter A. Chiabotti

(57) ABSTRACT

An electronically power-adjusted tattoo machine, power supply, and methods for controlling needle reciprocation are disclosed. The dynamic power adjustment controls needle impact force of a tattoo machine through electronic circuitry which establishes a baseline current of a tattoo machine motor, monitors current drawn by the motor, and increases or decreases the voltage provided to the motor as the current changes. The rate and degree of voltage adjustment may be varied by user-defined settings.

14 Claims, 18 Drawing Sheets

(56) References Cited

U.S. PATENT DOCUMENTS

| | | |
|---|---|---|
| 10,220,196 B2 | 3/2019 | Johansson |
| 10,265,482 B2 | 4/2019 | Jones |
| 10,471,246 B1 | 11/2019 | Lipscomb |
| 10,507,314 B2 | 12/2019 | Lee |
| 2005/0277973 A1 | 12/2005 | Huang et al. |
| 2009/0125049 A1 | 5/2009 | Copeland et al. |
| 2010/0072827 A1 | 3/2010 | Norstrom |
| 2010/0192730 A1 | 8/2010 | Dubin |
| 2010/0241151 A1 | 9/2010 | Rickard |
| 2011/0288575 A1* | 11/2011 | Colton ............... A61M 37/0076 606/185 |
| 2013/0096599 A1 | 4/2013 | Colton et al. |
| 2013/0138130 A1 | 5/2013 | Nizov |
| 2014/0094837 A1 | 4/2014 | Danenberg |
| 2016/0074645 A1 | 3/2016 | Siciliano |
| 2016/0256629 A1* | 9/2016 | Grosman ........... A61M 5/14244 |
| 2017/0007814 A1 | 1/2017 | Chan et al. |
| 2017/0157382 A1 | 6/2017 | Siciliano |
| 2017/0173319 A1 | 6/2017 | Mcguire et al. |
| 2017/0354810 A1 | 12/2017 | O'Brien, III |
| 2018/0000419 A1 | 1/2018 | Rassman |
| 2018/0043146 A1 | 2/2018 | Vescovi |
| 2018/0056054 A1 | 3/2018 | Siciliano |
| 2018/0200035 A1 | 7/2018 | Gagliano |
| 2018/0369553 A1 | 12/2018 | Siciliano |
| 2019/0134372 A1 | 5/2019 | Johansson |
| 2020/0038158 A1 | 2/2020 | Gagliano |
| 2020/0114137 A1 | 4/2020 | Siciliano |
| 2020/0121903 A1 | 4/2020 | Vester |

FOREIGN PATENT DOCUMENTS

| | | |
|---|---|---|
| CH | 704096 | 5/2012 |
| CN | 203219268 | 9/2013 |
| CN | 108042905 | 5/2018 |
| DK | 201770863 | 6/2019 |
| ES | 1173157 U | 12/2016 |
| ES | 1173159 U | 12/2016 |
| KR | 20170129685 | 11/2017 |
| KR | 20190091160 | 8/2019 |
| SG | 195416 | 12/2013 |
| WO | 2008146294 | 12/2008 |
| WO | 2015156715 | 10/2015 |
| WO | 2017189606 | 11/2017 |
| WO | 2017194336 | 11/2017 |
| WO | 2019096936 A1 | 5/2019 |
| WO | 2019106552 A1 | 6/2019 |

OTHER PUBLICATIONS

Patent Cooperation Treaty, "International Search Report" issued in International Patent Application No. PCT/US21/37837, dated Sep. 23, 2021; document of 7 pages.

* cited by examiner

| REFERENCE VOLTAGE | GIVE LEVEL | CURRENT (mA) | |
|---|---|---|---|
| | | BASELINE* | THRESHOLD |
| 6.0 | 0 | 71 | - |
| 6.0 | 1 | 70 | 112 |
| 6.0 | 2 | 69 | 106 |
| 6.0 | 3 | 68 | 100 |
| 6.0 | 4 | 70 | 97 |
| 6.0 | 5 | 70 | 92 |
| 6.0 | 6 | 69 | 86 |
| 6.0 | 7 | 68 | 80 |
| 9.0 | 0 | 69 | - |
| 9.0 | 1 | 70 | 112 |
| 9.0 | 2 | 69 | 106 |
| 9.0 | 3 | 69 | 101 |
| 9.0 | 4 | 69 | 96 |
| 9.0 | 5 | 68 | 90 |
| 9.0 | 6 | 69 | 86 |
| 9.0 | 7 | 67 | 79 |
| 12.0 | 0 | 81 | - |
| 12.0 | 1 | 78 | 120 |
| 12.0 | 2 | 80 | 117 |
| 12.0 | 3 | 82 | 114 |
| 12.0 | 4 | 77 | 104 |
| 12.0 | 5 | 84 | 106 |
| 12.0 | 6 | 83 | 100 |
| 12.0 | 7 | 83 | 95 |

FIG. 11

DEVICES AND METHODS FOR CONTROLLING NEEDLE RECIPROCATION

CROSS REFERENCE TO RELATED APPLICATIONS

This application claims priority to and the benefit of U.S. Provisional Patent Application No. 63/041,402, filed on Jun. 19, 2020, which is hereby incorporated by reference in its entirety.

BACKGROUND OF THE DISCLOSURE

The present disclosure generally relates to needling machines, such as tattoo, permanent makeup, and microneedling machines, and control over the speed of, or power delivered to, a needle and impact force of the needle into skin.

Tattoo machines, microneedling machines, and permanent makeup machines, among other needling devices, repetitively puncture skin as the needle is moved or dragged across the skin's surface. Shading or blending of pigments on a work surface is often achieved through a mechanical device between the needle and the motor that reduces the power translated from the motor to the needle tip, and thereby softens the impact of the needle to the skin.

While certain aspects of conventional technologies have been discussed to facilitate disclosure, Applicant in no way disclaims these technical aspects, and it is contemplated that the claimed disclosure may encompass one or more of the conventional technical aspects discussed herein.

In this specification where a document, act, or item of knowledge is referred to or discussed, that reference or discussion is not an admission that the document, act, or item of knowledge or any combination thereof was at the priority date, publicly available, known to the public, part of common general knowledge, or otherwise constitutes prior art under the applicable statutory provision; or is known to be relevant to an attempt to solve any problem with which this specification is concerned.

SUMMARY OF THE DISCLOSURE

The following presents a simplified summary of the disclosure in order to provide a basic understanding of some aspects of the disclosure. This summary is not an extensive overview of the disclosure. It is intended neither to identify key or critical elements of the disclosure nor to delineate the scope of the disclosure. Its sole purpose is to present some concepts of the disclosure, in accordance with the disclosure, in a simplified form as a prelude to the more detailed description presented later.

Embodiments of the present disclosure may include components manufactured from various materials based upon the contemplated use. For embodiments that are contemplated for human use, materials that are durable, cleanable or autoclaveable, and sanitary are contemplated to be within the scope of the present disclosure. By way of example and not limitation, materials may be stainless steel, anodized aluminum, and/or polycarbonates.

The present disclosure may address one or more of the problems and deficiencies of the prior art discussed above. However, it is contemplated that the disclosure may prove useful in addressing other problems and deficiencies in a number of technical areas. Therefore the claimed disclosure should not necessarily be construed as limited to addressing any of the particular problems or deficiencies discussed herein.

The following description and the annexed drawings set forth certain illustrative aspects of the disclosure. These aspects are indicative of only some of the various ways in which the principles of the disclosure may be employed, and the present disclosure is intended to include all such aspects and their equivalents. Other advantages and novel features of the disclosure will become apparent from the following description when considered in conjunction with the drawings.

Give adjustment in a tattoo machine may be accomplished by electronic control of the power supplied from power source of the tattoo machine to the tattoo machine motor. Electronic give adjustment emulates and replaces a mechanical system within a needling machine. The power signal of rotary direct current machines generally follows a wave form, either where the electrical potential is held at a specific voltage and the current drawn by the motor fluctuates, or the current is held at a specific amperage and the voltage fluctuates. A direct current motor in a needling machine can be controlled either by its voltage, its current, or both.

The electronic give control circuitry of the present disclosure first analyzes the particular power characteristics of a machine operating at a specific voltage set by a user to establish an average or baseline current. The voltage set by the user may define an upper voltage limit. A threshold current and lower voltage limit may then be established based on the power characteristics of the machine and voltage setting.

The actual current drawn by the motor may then be continuously monitored, iteratively, to determine if the observed current is above or below the threshold current. When the observed current exceeds the threshold current for the first time, the voltage may be lowered slightly from the upper voltage limit. Further subsequent current readings above the threshold further reduce the operating voltage iteratively. The process continues until either the lower voltage limit is reached (and that voltage is maintained so long as the current exceeds the threshold), or the current falls below the threshold, at which point the electronic give circuitry then starts to increase the voltage slightly and iteratively depending on the prior observed current (no hysteresis) or more than one prior observed currents (hysteresis). In this way, the circuitry is sensitive to the history of the observed current, which determines whether and to what degree the operating voltage of the machine is adjusted, either up or down between the upper voltage limit and the lower voltage limit.

Similar give emulation and control over the motor power (and thus the needle force) can likewise be achieved through setting a steady current, establishing a baseline voltage and threshold voltage, monitoring the voltage, and adjusting the current.

A give response for a machine can also be varied by a plurality of give levels, each give level having its own threshold and rate of change to the observed current exceeding or falling below the threshold current. In this way, a range of give emulations are possible, ranging from "hard" give to "soft" give.

BRIEF DESCRIPTION OF THE DRAWINGS

The disclosure can be readily understood by considering the following detailed description in conjunction with the accompanying drawings, in which:

FIG. 11 depicts a table of data of an embodiment of an electronic needling machine control system illustrating the relationship between the reference voltage, give level, baseline current, and threshold current.

DETAILED DESCRIPTION

Figure 1:
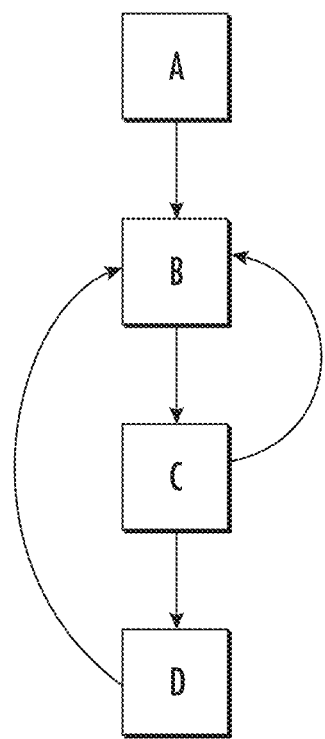
FIG. 1 illustrates a flowchart of an embodiment of a method of controlling a needling machine.

The following detailed description and the appended drawings describe and illustrate various embodiments of the disclosure solely for the purpose of enabling one of ordinary skill in the relevant art to make and use the disclosure. As such, the detailed description and illustration of these embodiments are purely exemplary in nature and are in no way intended to limit the scope of the disclosure, or its protection, in any manner. It should also be understood that the drawings are not to scale and in certain instances details have been omitted, which are not necessary for an understanding of the present disclosure, such as conventional details of fabrication and assembly.

In the Summary above, in the Description, and in the accompanying drawings, reference is made to particular features of the disclosure. It is to be understood that the disclosure in this specification includes all possible combinations of such particular features. For example, where a particular feature is disclosed in the context of a particular aspect or embodiment of the disclosure, or a particular claim, that feature can also be used, to the extent possible, in combination with and/or in the context of other particular aspects and embodiments of the disclosure, and in the disclosure generally.

The term "comprises" and grammatical equivalents thereof may be used herein to mean that other components, structures, steps, etc. are optionally present. For example, an article "comprising" (or "which comprises") components A, B, and C can consist of (i.e., contain only) components A, B, and C, or can contain not only components A, B, and C, but also one or more other components or structures.

Unless otherwise specified, the term about" when used in the context of a numeric figure may be defined to mean±20% of the corresponding number(s). The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

While the specification will conclude with claims defining the features of embodiments of the disclosure that are regarded as novel, it is believed that the disclosure will be better understood from a consideration of the following description in conjunction with the figures.

A particular needling machine, including its motor, needle cartridge, motion translation and other mechanical features, may have unique power requirements. And even within a particular machine setup, those power requirements can change depending on whether a user selects a different operating voltage with the same mechanical components, or changes mechanical components, such as changing to a different needle cartridge, machine grip, and/or other component.

For each machine set up for a particular needling machine, the electronic give circuitry establishes an average current drawn by the motor. Where the electric signal comprises a waveform, several measurements of the current may be taken to identify the average current. In certain embodiments, about five observations of the current may be sufficient to establish the average current, and, in a preferred embodiment, ten observations over one cycle of the waveform may establish the average current. In other embodiments, any desired number of observations may be utilized to establish the average current.

In certain embodiments, an incremental averaging process may be employed to establish the baseline average current. In one embodiment, the electronic circuitry includes five current variables. The observed current and the first current variable are averaged, and the resulting value then becomes the first current variable. A second current variable is then averaged with the prior (now averaged) first current variable, and the resulting value then becomes the second current variable. A third current variable is then averaged with the prior (now averaged) second current variable and a fourth (not yet averaged in the current iteration) current variable. The average of those three values is then overwritten in the electronic circuitry and becomes the third current variable. In this way, the prior iteration of the averaging sequence is fed back into the present averaging iteration based on the observed current. The fourth current variable is then averaged with the prior (now averaged) third current variable, and the resulting value then becomes the fourth current variable. A fifth current variable is then averaged with the prior (now averaged) fourth current variable, and the resulting value then becomes the fifth current variable. This averaging process continues for each observed machine current for a minimum of five iterations. At the end of the iterations, the fifth (now fully iteratively averaged) variable is the final baseline current of the machine. In certain embodiments, other amounts of current variables may be used with the electronic circuitry.

The averaging may be varied among the current variables. For example, the feedback averaging may be included in the first current variable, with the prior iteration second variable together with the observed current. The other current variables may then follow the non-feedback averaging process.

In a preferred embodiment, the number of iterations (observed current values) may be about thirty-two. In certain embodiments, the number of observed current averaging iterations may depend on the temporal resolution of the current sensor. In a preferred embodiment, about six periods each having about five observations may be utilized to establish the baseline current. In other embodiments, one full period of the waveform may be sufficient to establish the average current provided that there are a sufficient number of current observations over the waveform period. A sufficient number of current observations in a single waveform period may be between about five and ten. The system may establish the threshold current reasonably quickly, and therefore a maximum number of operational current values that are read during establishment of the baseline official currents may be about fifty.

Biasing the current variables may further improve accuracy of the baseline current, or may allow for faster establishment of the baseline. In a preferred embodiment, the baseline current variables have a pre-set value of about eight-five milliamps.

The baseline current may be established before the machine encounters the work surface (e.g. a user's skin or the skin of a client) so that the true baseline operational parameters of the machine can be determined. However, some embodiments may include incorporating and utilizing memory in the circuitry and component-identifying features that can determine the specific machine, specific power source, and/or other characteristics of a device's setup, and/or the general make and model of component or machine, such that a previously-established baseline can either be recalled from memory without reestablishing the baseline, or the starting bias of the current variables can be adjusted for more rapid acquisition of the baseline.

The baseline current may also reestablished by the electronic circuitry in response to specific triggering events. In a preferred embodiment, a user changing the reference voltage at which a machine operates may automatically result in the electronic circuitry reestablishing the baseline current. Turning the machine on (supplying power to the motor) may also result in immediately establishing the baseline. Changing the power source may also trigger the circuitry to reestablish a baseline, such as swapping a disconnectable discharged battery for a charged battery unit. A manual reset option may also be provided in the circuitry to allow a user to reestablish the baseline, such as when a more viscous ink or substance is applied to the needle.

A needling machine may be set and its reciprocation speed adjusted according to a specific electrical potential or voltage. That reference voltage may be set by a user, and may also be the voltage at which the machine operates without any give control feedback or voltage adjustment. The reference voltage may also define the upper limit of a range of voltage at which the machine will operate when the electronic give control circuitry is triggered.

A voltage error range may be provided in some embodiments to account for observational error of the observed voltage to prevent unwanted voltage fluctuation or adjustment.

Additionally, the reference voltage may further define a lower limit of the range of voltages at which the machine will operate with the electronic give control. The lower limit may be established as a percentage (or fraction) of the reference voltage. In some embodiments, the lower voltage limit may be about two-thirds of the reference voltage. In other embodiments, the lower voltage limit may be another fraction of the reference voltage.

In certain embodiments, the lower limit on the range of voltage may be established at an absolute number. In some embodiments, the absolute lower limit of the voltage range is 4.5 V. In still other embodiments, the lower limit of the voltage range may be established by the greater of the percentage of the reference voltage or an absolute number.

Separate from the reference voltage, which may be stored in a memory of the electronic circuitry, is an operating voltage. The operating voltage may define the voltage at which the machine will operate at a given moment in time depending on the historical current drawn by the motor of the needling machine. The operating voltage may be set in a voltage regulator within the electronic circuitry such that the electronic circuitry controls the provision of power from a power source to the machine motor.

The electronic circuitry may also be configured to have one or more settings defining the parameters under which the electronic circuitry adjusts the voltage provided to the motor. In a preferred embodiment, the one or more settings is a give level. In some embodiments, the give level may range from zero to seven, with zero representing no voltage adjustment (i.e. normal operation of the machine without give adjustment), one emulating a "hard" give, seven emulating a "soft" give, and the levels between one and seven ranging from the hardest give to the softest give. Some embodiments may include greater or fewer give levels. For example, the give level range may range from zero to five or to any number. In certain embodiments, the give level may range from a number other than zero to any other desired number. In one embodiment, the give level may be binary (on or off). In certain embodiments, the give levels may range from zero to about twenty.

Based on the baseline current and the user-selected give level, the electronic circuitry may establish a threshold current greater than the baseline current. The difference from the baseline current to the threshold current, ΔI (delta I), may correspond to the give level selected. In a preferred embodiment, ΔI is the sum of five times the give level, plus about 42 milliamps (a variable stored in memory that may be identified as a GIVE_RANGE). In other embodiments, ΔI may range from adding between about 30 milliamps and about 60 milliamps. In still other embodiments, ΔI may range from between about two to about ten times the give level. In still other embodiments, ΔI may be determined by a combination of a multiple of the give level plus a specific amount of current.

In operation, the electronic circuitry continuously monitors the operational current drawn by the motor and evaluates the observed current against the threshold current. Where the current exceeds the threshold current, the electronic circuitry then may evaluate the operational voltage against the reference voltage. Where the observed machine current is below the threshold current, but the operational voltage is approximately equal to the reference voltage, no voltage adjustment may be made. Under these conditions, the machine may operate within the parameters defined by the reference voltage and give level set by the user, without any adjustment to the operational voltage. This operational state may be considered a maximum-power state where no give adjustment to the operational voltage is made. Where the observed machine current exceeds the threshold current and the operational voltage is above the lower voltage limit, the electronic circuitry may begin to incrementally decrease the operational voltage. This operational state may be considered a power-decrease state. A subsequent observed machine current above threshold results in a further incremental decrease in operational voltage. Where the observed current fluctuates around the threshold, little or no change to the operational voltage may result. This operational state may be considered a steady state. When an observed machine current is below the threshold current and the operational voltage is less than the reference voltage, the electronic circuitry may begin to incrementally increase the operational voltage. This operational state may be considered a power-increase state. Subsequent observed machine current below the threshold results in a further incremental increase in operational voltage. A fifth operational state may exist where the electronic circuitry maintains the operational voltage at about the lower voltage limit as a result of continued operational current readings exceeding the threshold current. This may be considered a minimum-power state. The electronic circuitry may continuously and iteratively allow the machine to vary from state to state, depending on the observed current drawn by the motor and the operational voltage.

In some embodiments, the electronic circuitry may increase the degree to which the operational voltage is decremented upon subsequent observed machine currents exceeding the threshold, and similarly may increase the degree to which the operational voltage is incremented upon subsequent observed machine currents falling below the threshold. In this way, and in such embodiments, the electronic circuitry results in accelerated change of voltage the longer the observed machine current remains above or below the threshold over time. In other embodiments, the electronic circuitry may be configured to acceleratingly reduce the operational voltage, but provide a more rapid voltage recovery (increase) upon the machine current falling below the threshold.

In a preferred embodiment, the electronic give circuitry may include a hysterical evaluation of the degree to which the voltage is adjusted based on the history of prior observed current readings. In one embodiment, the electronic circuitry may adjust the voltage only after at least two consecutive observations of current exceeding the threshold current. Similarly, the circuitry may likewise only increase the voltage only after at least two consecutive observations of current being below the threshold current. Other embodiments may include no hysteresis, and instead the electronic circuitry may adjust the operational voltage immediately upon and observed current being above or below the threshold current, and further depending upon the operational voltage prior to making the adjustment (that is, the then-existing operational voltage prior to adjusting the voltage). For example, when the machine operating voltage is equal to the reference voltage, observed current below the baseline would not result in a change in operational voltage because the motor is already operating at the upper limit (reference) voltage.

In a preferred embodiment, the electronic give circuitry may be housed within the machine, maintaining direct electrical contact with the motor, and disconnectable electrical contacts with a power supply. In other embodiments, the electronic give circuitry may be housed within a detachable battery pack, with disconnectable electrical contact with the motor. In still other embodiments, the majority of the electronic give circuitry may be housed within a power controller separate from the machine and power source, being in communication with a voltage regulator either within the machine or within the power source. In certain embodiments, the electronic give circuitry may be housed within any of the components of the machine, disconnectable components of the machine, or a combination thereof.

In certain embodiments, the machine and/or the disconnectable components that may be connected to the machine may be configured to house any number of communications devices, such as, but not limited to, communications modules, radios, wireless chips, cellular chips, short-range wireless chips, long-range wireless chips, transceivers, any other type of communications device, or a combination thereof. In some embodiments, the communications radio(s) and/or other communications devices may operate as both master or slave relative to the machine, disconnectable power sources, and other peripheral devices, such as a foot switch.

Now, with reference to FIG. 1, a flowchart of a method of an embodiment of the present disclosure is illustrated. In certain embodiments, any one or more of the steps may be performed by a processor of a needling device, tattoo machine, or a combination thereof. In certain embodiments, the one or more steps of the method may be performed be devices connectable to the needling device and/or tattoo machine. In certain embodiments, the steps of the method may be performed in the order as shown in FIG. 1, however, in other embodiments, one or more steps may be performed in different orders with respect to each other. Additionally, in certain embodiments, the method of FIG. 1 may be combined with any of the other methods described herein and may incorporate any of the functionality described in the present disclosure. At step A, the method may include establishing a threshold current and a voltage range for a needling machine. The method may proceed to step B, which may include comparing the observed operational current for the needling machine to the threshold current. The method may proceed to step C, which may include evaluating the operational voltage in comparison to the voltage range. When the operational current is below the threshold current, and the operational voltage is within an error limit of the maximum voltage, the method may return to step B, and no adjustment to the operational voltage may be made. However, where the operational current exceeds the threshold current, and the operational voltage is above the voltage minimum, the method may proceed to step D, which may include adjusting the voltage downward from the then-existing operational voltage. Similarly, where the operational current is below the threshold current and the operational voltage is below the maximum voltage, the method may include, at step D, adjusting the voltage upward from the then existing operational voltage. In certain embodiments, after any adjustment up or down in the operational voltage, the method may then return to step B and continue through the steps of the method. Notably, the steps of the method may be repeated continuously over time as the needling device and/or tattoo machine operates over time. In certain embodiments, the method of FIG. 1 may be combinable with features and functionality provided by other methods disclosed in the present disclosure, systems disclosed in the present disclosure, and machines and devices disclosed in the present disclosure.

Figure 2:
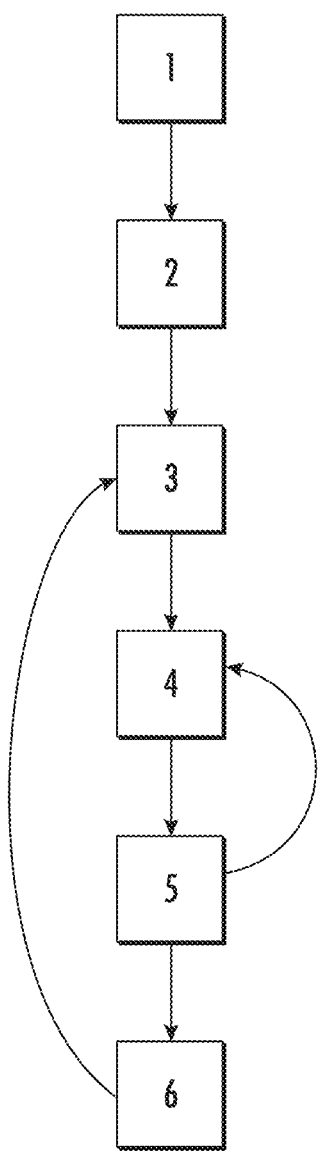
FIG. 2 illustrates a flowchart of another embodiment of a method of controlling a needling machine.

FIG. 2 illustrates a flowchart depicting steps of an additional embodiment of the present disclosure. At step 1, the method may include setting a reference voltage for a machine (e.g. needling machine, tattoo machine, etc.), and from that reference voltage establishing a minimum and maximum voltage for the machine. In certain embodiments, a user may set the reference voltage, however, in certain embodiments, the reference voltage may be set by one or more components of a needling machine and/or tattoo machine, such as, but not limited to, a processor of the needling machine and/or tattoo machine. In certain embodiments, a remote device communicatively linked to the needling machine and/or tattoo machine may set the reference voltage as well. The method may proceed to step 2, which may include establishing a threshold current based on a plurality of observed current values in the system (i.e. needling machine control system, other systems described herein, the tattoo machine, and/or needling machine) operating at the reference voltage. At step 3, the method may include setting the operational voltage for the machine. Initially, the operational voltage may be set to the reference voltage. The method may proceed by monitoring the current and comparing the current to the threshold current in step 4. Subsequently, the operational voltage may be compared to the minimum and maximum voltages in step 5. When the operational current is below the threshold current, and the operational voltage is near the maximum voltage, the method may proceed back to step 4. However, when the operational current exceeds the threshold current and the operational voltage is above the voltage minimum, and when the operational current is below the threshold current and the operational voltage below the maximum voltage, the method may proceed to step 6, which may include adjusting the operational voltage either up or down, and then setting the new operational voltage at step 3. The method may continuously loop through steps 3 through 6 iteratively for each current observed by the system. In certain embodiments, the systems described in the present disclosure may perform any one or more of the steps of the method of FIG. 2.

Figure 3:
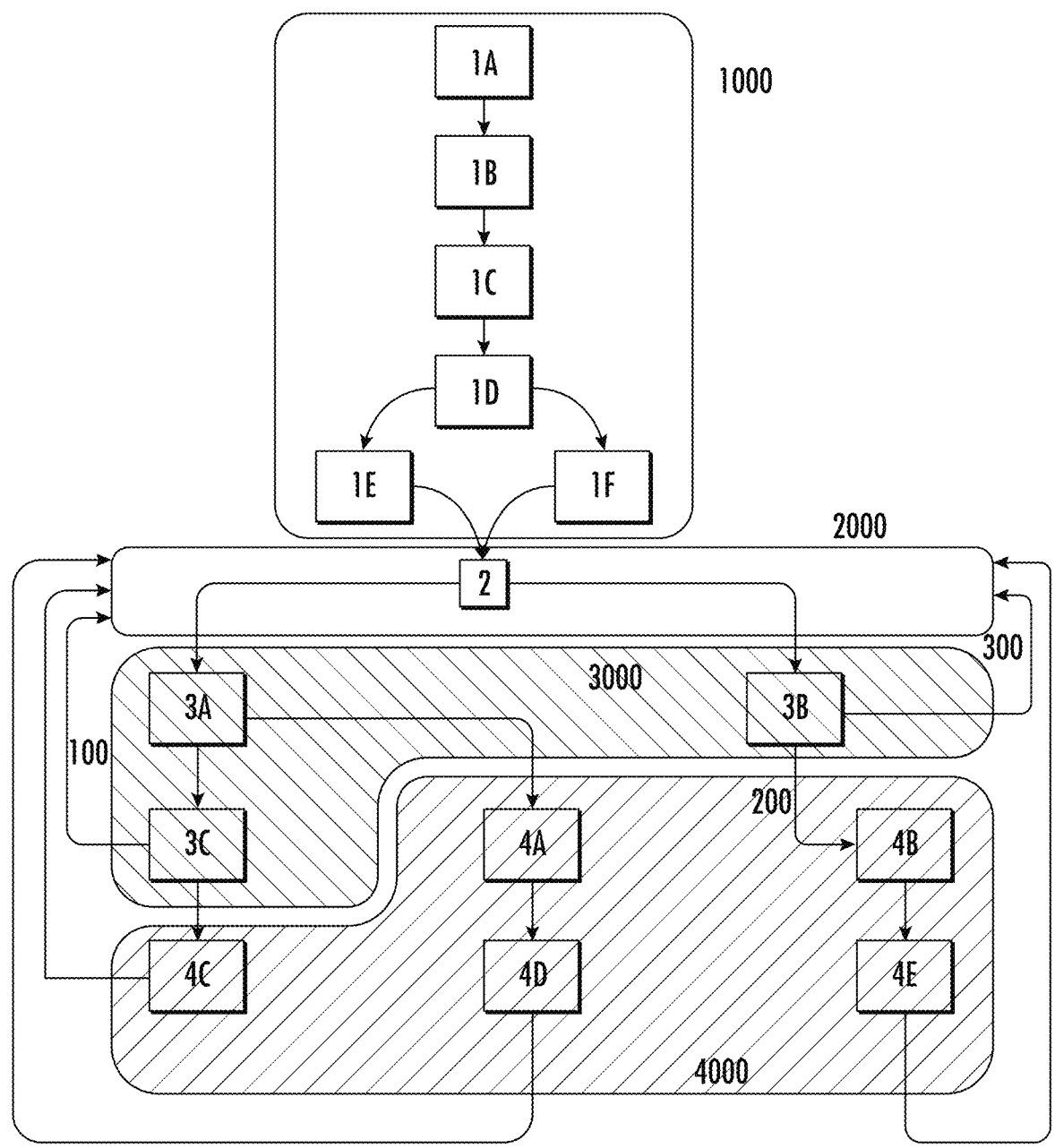
FIG. 3 illustrates a flowchart of still a further embodiment of a method of controlling a needling machine.

Now, with reference to FIG. 3, a flowchart depicting a method providing the logical operations of the electronic circuitry and steps resulting in needle machine give emulation is disclosed. The operations may be method operations, system operations, or a combination thereof. In certain embodiments, the system may include a needle machine and/or tattoo machine configured to perform the operative steps of the method as well. Within initialization stage 1000, the method may include setting a reference voltage and give level for a needling machine at step 1A, those values being stored in a memory. In certain embodiments, the reference voltage may be set by a user, however, in certain embodiments, the reference voltage may be set via device or component communicatively linked to the needling machine. That reference voltage may then be set as the operational voltage at step 1B in a voltage regulator or power controller included as part of the electronic circuitry of the needling machine. The needling machine may then be supplied power at the operational voltage, and at step 1C, the electronic circuitry may monitor the current drawn by the motor electrically connected to the voltage regulator or power controller. From that observed current, a baseline or average machine current may be established. Step 1D of the method may include evaluating the baseline current and then categorizing the machine at steps 1E or 1F according to the machine's baseline current. As that final step in the initialization stage 1000, the method may include establishing a threshold current based on the baseline current and the give level, and storing the threshold current in memory. Greater or fewer categories of machines may be provided in additional alternative categorization steps similar to steps 1E and 1F prior to advancing out of the initialization stage 1000 and into current evaluation stage 2000. However, in certain embodiments, only one threshold current may be established as a result of the initialization stage 1000.

As indicated above, the method may proceed to the current evaluation stage 2000, which may include, at step 2, comparing the threshold current against the machine's operational current. If the observed current is below the threshold current, then the method may proceed into voltage evaluation stage 3000 and more specifically to step 3A. If the observed current is not below the threshold current, the method may advance into voltage evaluation stage 3000, but, instead of advancing to step 3A, the method may advance to step 3B.

At step 3A, the method may include comparing the operational voltage of the machine to the reference voltage. When the operational voltage is not below the reference voltage (within an error range of the reference voltage), a second voltage evaluation occurs at step 3C, an upper voltage limiter At step 3C, the method may include determining whether the operational voltage is above the reference voltage (within the error range). If the operational voltage is not above the reference voltage, the method may proceed back to step 2 via return 100 without a change in the operational voltage. This is because the system including the machine is not experiencing an increase in current and is also at maximum voltage. But when the operational voltage is above the reference voltage, the method includes proceeding to voltage adjustment stage 4000, and step 4C more specifically.

At step 4C, the method includes decreasing the operational voltage statically, and ensuring a return of the operational voltage subsequent to a series of increasing voltages at step 4D. From step 3A, whether the operational voltage is below the reference voltage, the method progresses into voltage adjustment stage 4000, and step 4A more particularly. At step 4A, the method may include having the circuitry set a ramp-down factor to a default value, and also set a ramp-up factor based on the number of times the method (or system) has consecutively iterated through to step 4A. Once the ramp-up factor is set, the method (and/or system) may include evaluating the increment in voltage based on the ramp-up factor and the then-existing operational voltage. The method may then include setting the new (higher) voltage in the voltage regulator or power controller and the method (and/or system) may return to step 2 of the current evaluation stage 2000.

In certain embodiments, an alternative sequence from step 2 may result in a decrease in operational voltage. When the observed current is above the threshold current, the method (and/or system) may include advancing into voltage evaluation stage 3000 at step 3B. Step 3B of the method may include evaluating whether the operational voltage is above the greater of two-thirds of the reference voltage or 4.5 volts. If the operational voltage is not above the greater of two-third of the reference voltage or 4.5 volts, the method (and/or system) may proceed back to step 2 via return 300 without a change in the operational voltage because although there is an increase in current, the machine (and/or system including the machine) is operating at the lower voltage limit.

When the voltage is not at the lower limit, the method (and/or system) may advance into voltage adjustment stage 4000. At step 4B, the method may include having the electronic circuitry set the ramp-up factor to a default value, and also set the ramp-down factor based on the number of times the method (and/or system) has consecutively iterated through to step 4B. Once the ramp-down factor is set, the method (and/or system) may evaluate the decrement in voltage based on the ramp-down factor and the then-existing operational voltage. The method may then include setting the new (lesser) voltage in the voltage regulator or power controller and the method (and/or system) may return to step 2.

As a result of the feedback of the system across the current evaluation stage 2000, voltage evaluation stage 3000, and voltage adjustment stage 4000, the method may include having the circuitry continuously and dynamically adjust the operational voltage between the upper voltage limit and the lower voltage limit according to each observed machine current. In certain embodiments, hysteresis may be added to voltage adjustment stage 4000 by evaluating the value of the ramp-up factor or the ramp-down factor. Because the more times the method (and/or system) consecutively iterates steps 2→3B→4B→4E→2 (ramp-up loop), or iterates steps 2→3A→4A→4D→2 (ramp-down loop) the greater the corresponding ramp-up or ramp-down factor is, an additional check on the value of the ramp factor can either advance the method (and/or system) to the voltage corresponding adjustment step (4D or 4E) once a minimum number of iterations has occurred, or return to step 2. For example, the method (and/or system) may require at least two iterations through the ramp-down loop before actually lowering the operational voltage. In this way, the method (and/or system) can prevent rapid oscillation of the operational voltage where the observed current continuously oscillates above and below the threshold current. In certain embodiments, other numbers of iterations through the ramp-down loop may also be specified as a trigger for lowering the operational voltage.

Figure 4:
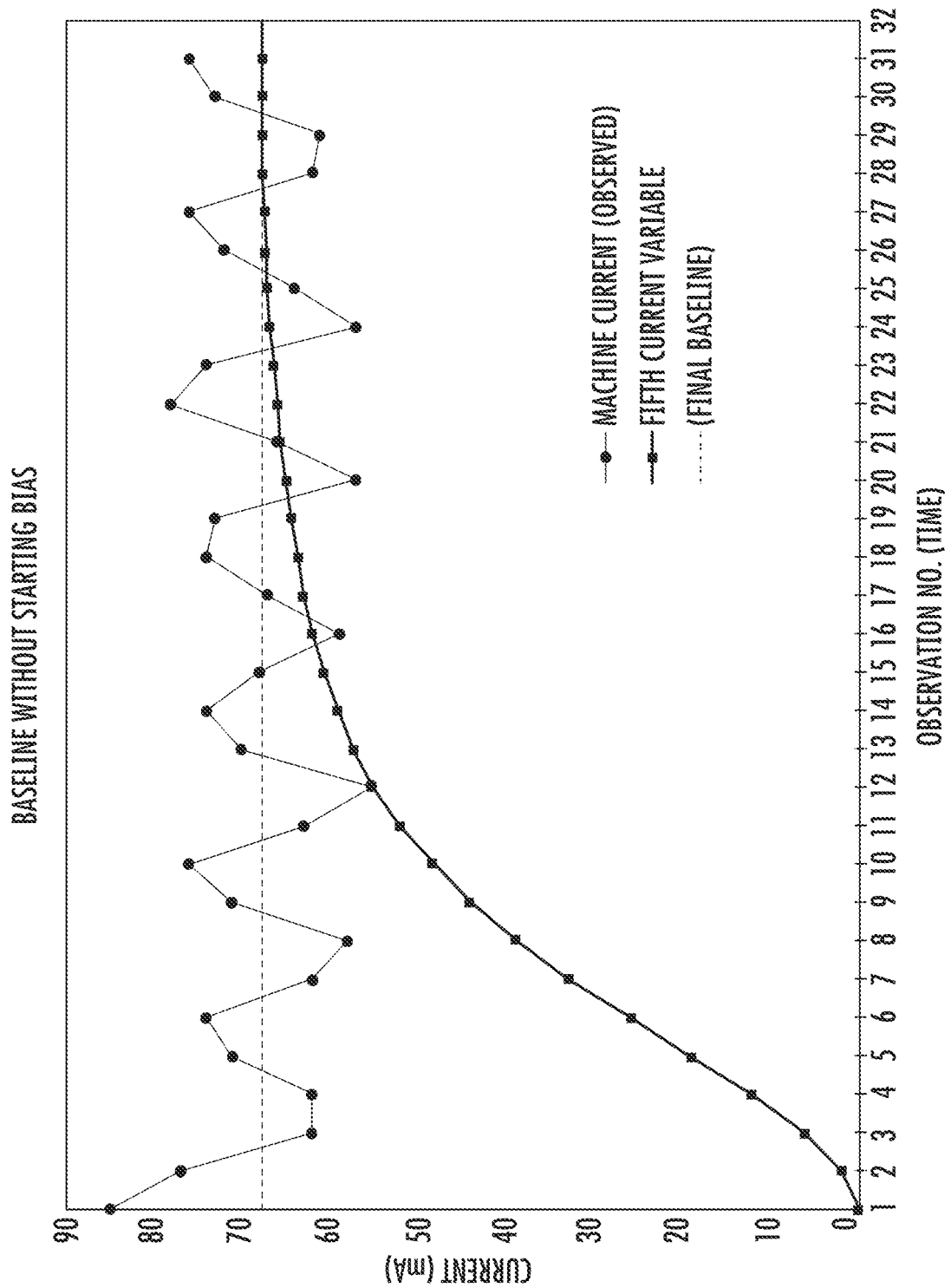
FIG. 4 illustrates the acquisition of a baseline current of a needling machine in an embodiment of needling machine electronic circuitry.
Figure 5:
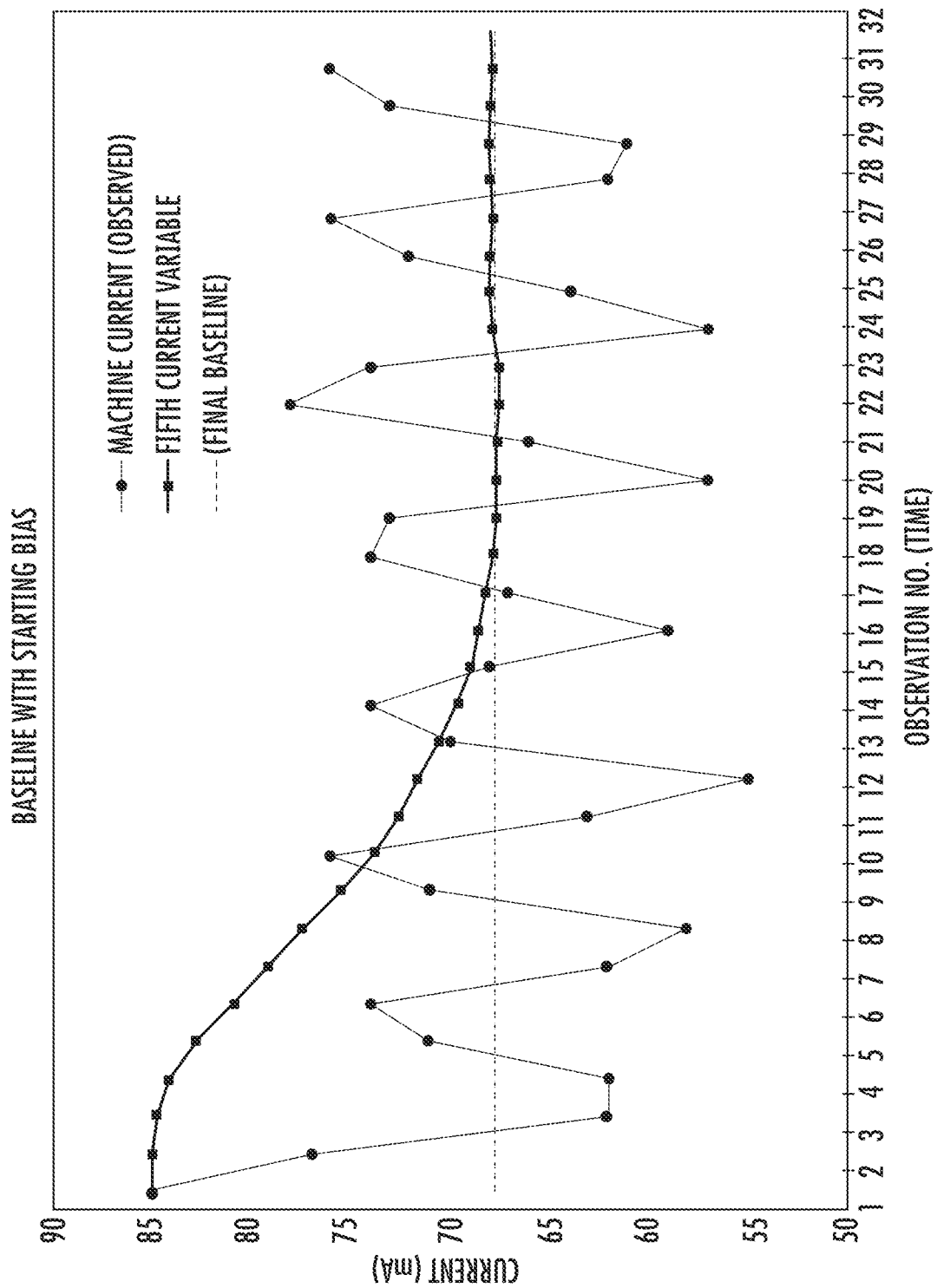
FIG. 5 illustrates the acquisition of a baseline current of a needling machine in an alternative embodiment of needling machine electronic circuitry.

Turning now to FIGS. 4 and 5, graphical illustrations depict how the baseline of a machine (e.g. needling machine, tattoo machine, therapeutic machine, or other machine) can be determined from an irregular current waveform. As shown, the observed machine current varies across time. At each observation, the current value may range, but it does so approximately sinusoidally. As shown in FIG. 4, an averaging process with feedback (showing only the fifth current variable, as an example) quickly results in an approximation of the motor's current within about 27 observations across about 7 periods of the waveform. In this embodiment, the five current variables do not begin the averaging process with a specific value, but instead are either zero or null. In certain embodiments, the same iterative averaging process may establish a motor's baseline current more rapidly with a starting bias value assigned to each of the current variables, as depicted in FIG. 5. Beginning the averaging process with a value of 85, the system achieves the baseline current after only about 18 observations across about 5 periods. In other embodiments, different beginning averaging process values may be utilized, which may result in varying numbers of observations for the system to achieve the baseline current.

Figure 6:
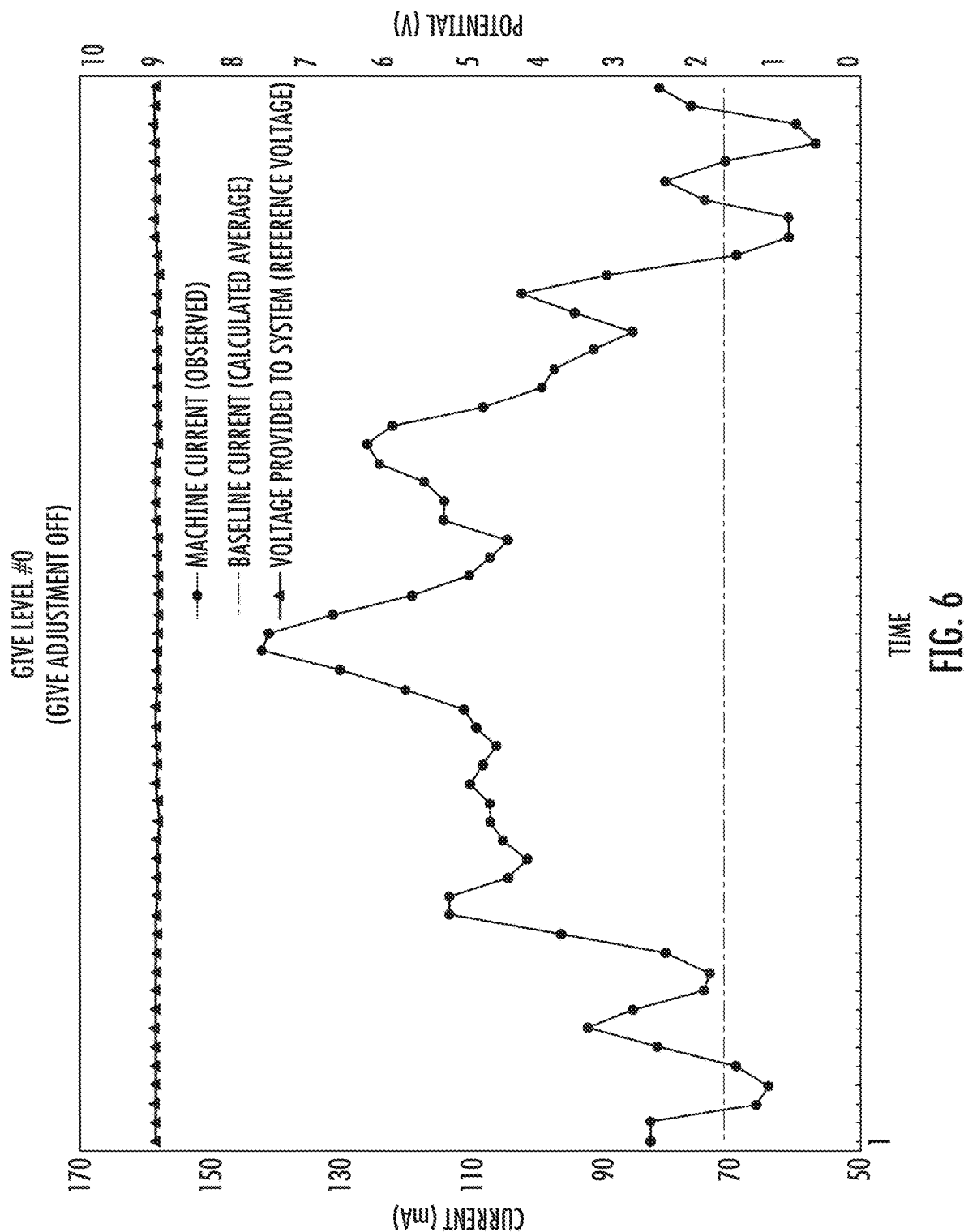
FIG. 6 illustrates the relationship between a reference voltage and electrical current drawn by a needling machine motor in an embodiment of a needling machine electronic circuitry in which the give adjustment is off.

Without the electronic give adjustment, a needling machine would operate under its normal conditions by drawing more current as the system attempts to keep the voltage constant. FIG. 6 illustrates such no-give conditions. As can be seen visually in FIG. 6, the current value over time does not have the type of sinusoidal patterns as shown in FIGS. 4 and 5, which involve utilizing electronic give adjustments.

Figure 7:
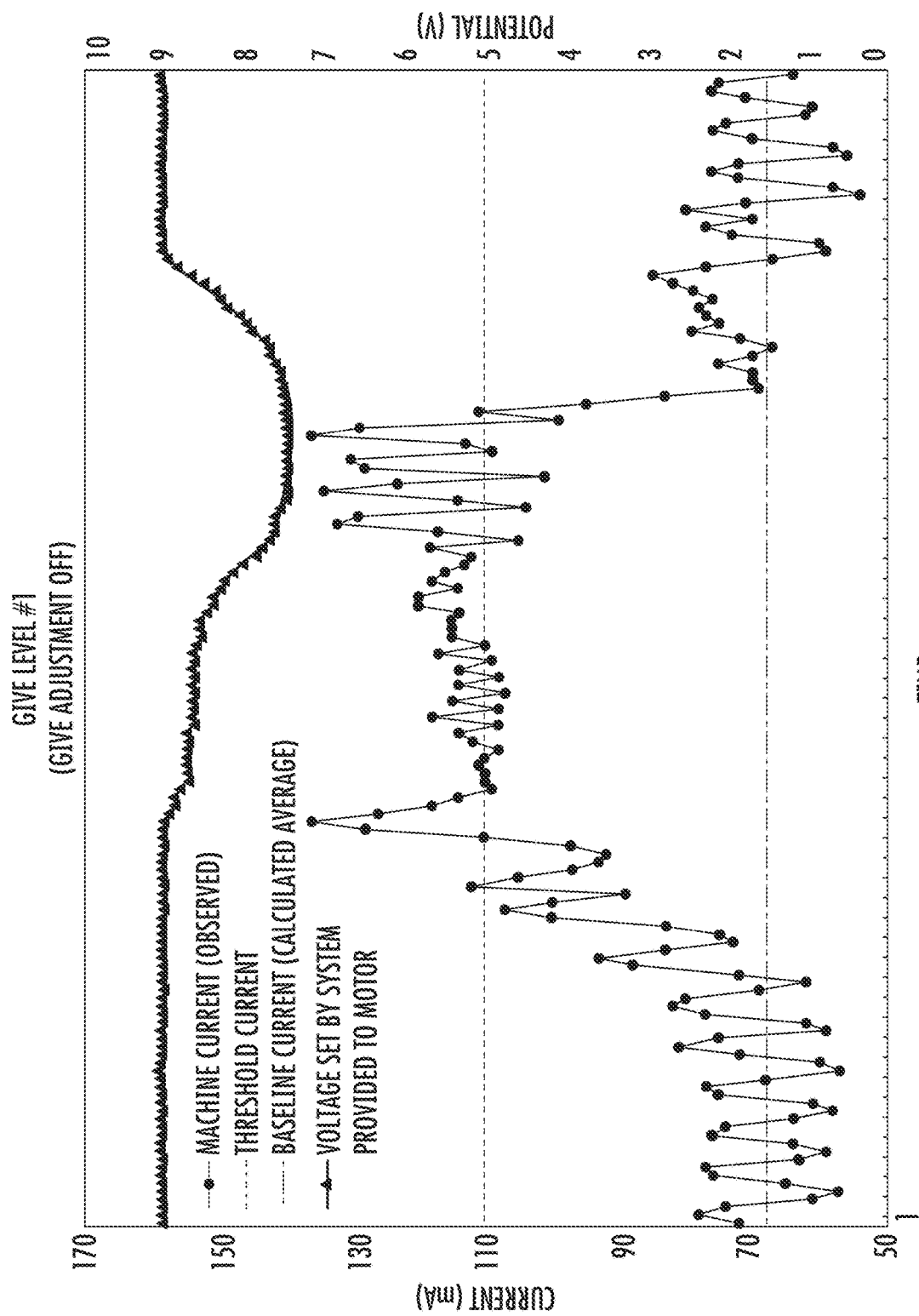
FIGS. 7, 8, and 9 illustrate the relationship between a reference voltage and electrical current drawn by a needling machine motor in an embodiment of a needling machine electronic circuitry in which the give adjustment varies from 1 to 4 to 7, respectively.
Figure 8:
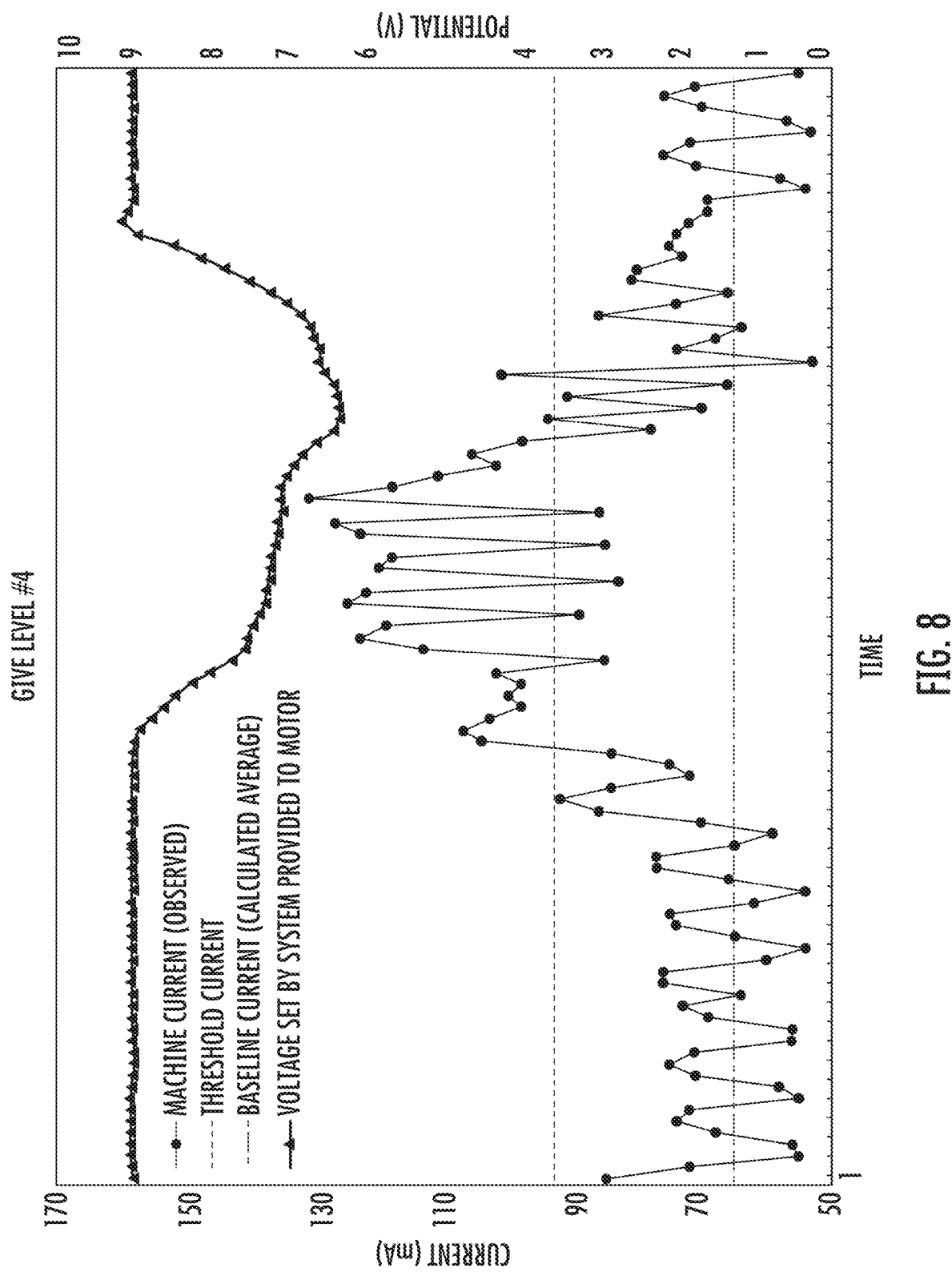
Figure 9:
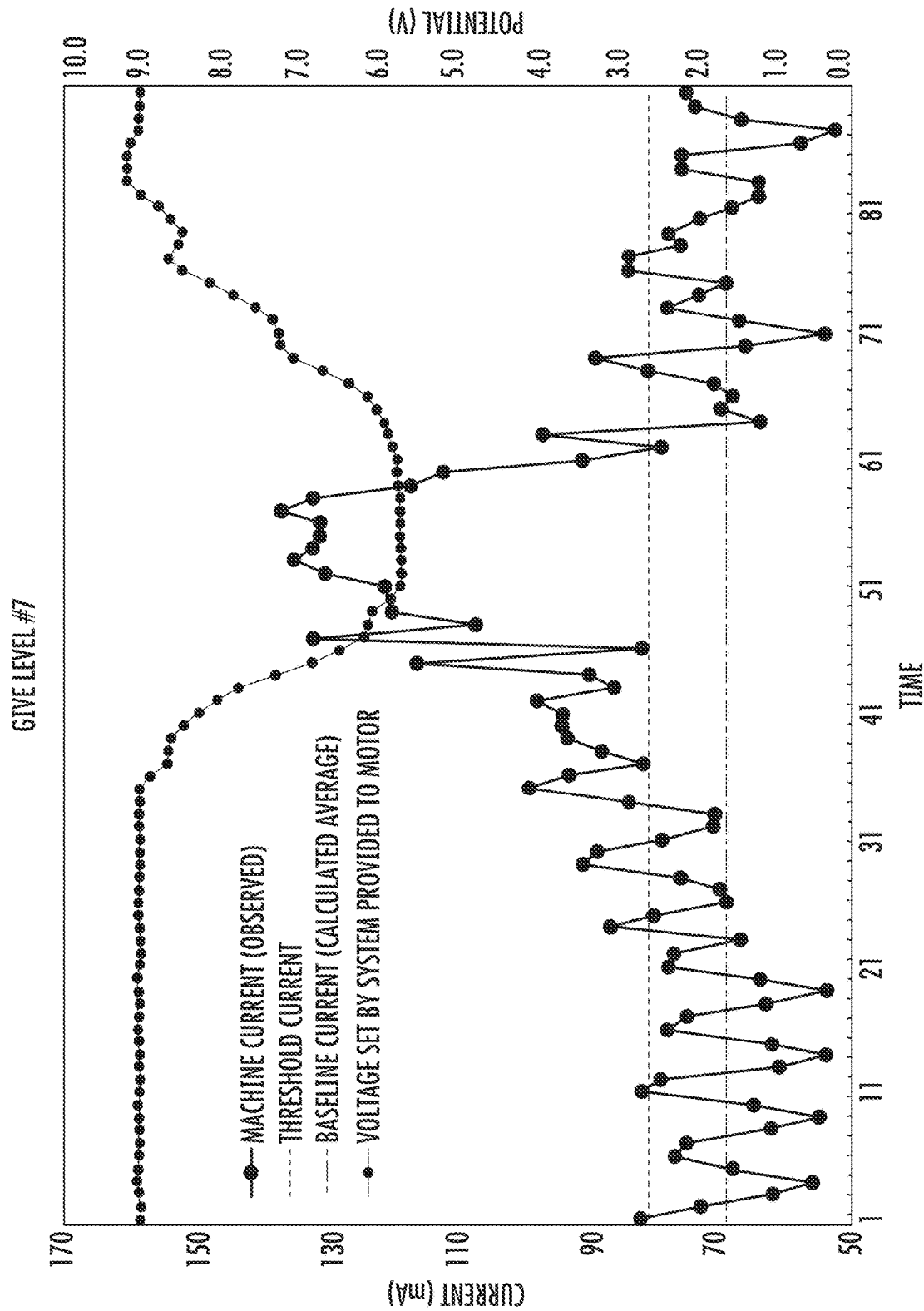

FIGS. 7, 8, and 9, on the other hand depict how the machine's voltage may be adjusted in response to a change in current and in the context of varying give levels, which, for example, may range from zero to seven. In certain embodiments, at give level zero, there may not be a threshold current. In certain embodiments, starting at give level one, the threshold current may decrease with each subsequent increase in give level up to give level seven. In other words, give level one may have a higher threshold current than the threshold currents for give levels two, three, four, five, six, and seven. Each figure depicts a baseline operating condition, showing oscillating observed machine current with a steady-state operational voltage until the observed machine current exceeds the threshold current, after which point the system responds by lowering the operational voltage slightly. Subsequent current observations above the threshold lead to an increasing degree of change of the operating voltage as the system lowers the power, but preventing the voltage from falling below the lower voltage limit.

With reference to FIG. 7, an embodiment of the present disclosure affects the operating voltage for the machine according to a give level of one. A give level of one may correspond to a "hard" give. In certain embodiments, the threshold current may be set considerably higher than the baseline current. Consequently, a larger increase in current is required to trigger the system and thereby lower the operational voltage. When the current continuously remains above the threshold, the faster the operational voltage may be decreased. However, when the observed machine current is high, yet oscillates occasionally below the threshold current, the rate of voltage change may be slowed down. Similarly, once the observed current falls below the threshold current, the system may recover the power up to the normal operating state by increasing the voltage to a greater and greater degree the longer the current is continuously below the threshold.

FIG. 8 illustrates how an embodiment of the present disclosure affects the operating voltage according to a medium give level of four. With a slightly lower threshold current than give level one in FIG. 7, give level four in FIG. 8 also shows how the operational voltage lower limit is lower than the limit provided with a give level set at one. With a high rate of increase in the operational voltage during a power-up loop, the system may initially exceed the maximum voltage level slightly on the last voltage increase iteration, as shown in FIG. 8. However, the system may include an alternative monitoring process to ensure that the operational voltage returns to the maximum (reference) voltage.

FIG. 9 depicts an embodiment of an even softer give level of seven. The graph in FIG. 9 depicts an even lower threshold current than the threshold currents utilized in FIGS. 7 and 8, which triggers a decrease in power more quickly than the embodiments of FIGS. 7 and 8 as the machine encounters resistance on a work surface, such as a user's skin. Similarly, when the observed current falls below the threshold current, the system may increase the power more quickly than in other embodiments where the threshold current is higher than the embodiment of FIG. 9.

Figure 10:
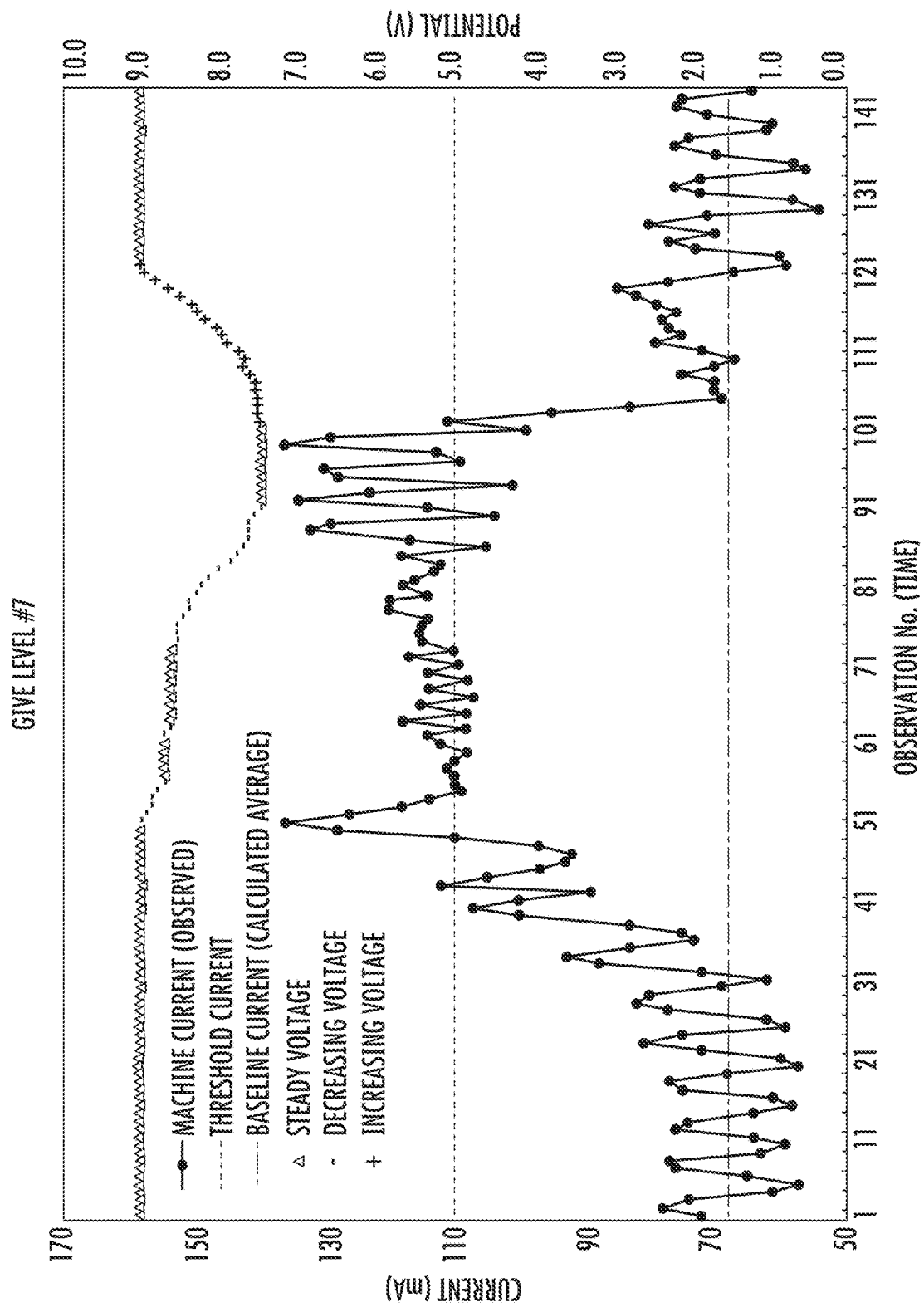
FIG. 10 illustrates the various states of voltage control exerted by the give control electronic circuitry over a needling machine according to the observed machine current in relationship to the baseline current and the threshold current.

In these embodiments, the system may provide a smooth transition from a maximum power state to a decreasing power state, from a minimum power state to an increasing power state, and from an increasing power state back to the maximum power state. FIG. 10, for example, illustrates operational states of the system, including steady voltage (whether at the maximum, minimum or middle voltage), decreasing voltage, and increasing voltage.

Turning now to FIG. 11, a table is provided, which illustrates an embodiment of the numerical relationship between a user-set reference voltage, a plurality of user-set give levels (settings) at a particular reference voltage, the baseline current for a particular initialization sequence, and the corresponding threshold resulting from the give level and baseline all for a single (the same) physical machine configuration. For a give level setting of 0, regardless of the reference voltage, the control circuitry may not establish a threshold current since the voltage adjustment functionality provided by the circuitry does not operate while the system is set to have no give adjustment. However, at increasing give levels between 1 and 7, the corresponding threshold current (again, being dependent on the baseline current) may decrease. Although the components of a machine setup may not may vary during a change from one reference voltage to another, the baseline current established at each initialization stage may vary slightly from run-to-run. In preferred embodiments, the error range of the baseline current, run-to-run, should be within ±5% for stable operation of the system and usability across varying machines and setups. As can also be discerned from the data contained in FIG. 11, as the reference voltage increases, the baseline current may also increase. However, the data represented in the table of FIG. 11 is for illustrative purposes only, and the actual reference voltage suitable for a given machine or set up may vary from between about 3 volts to about 18 volts, depending on the power requirements and configuration of the motor and machine.

Figure 12:
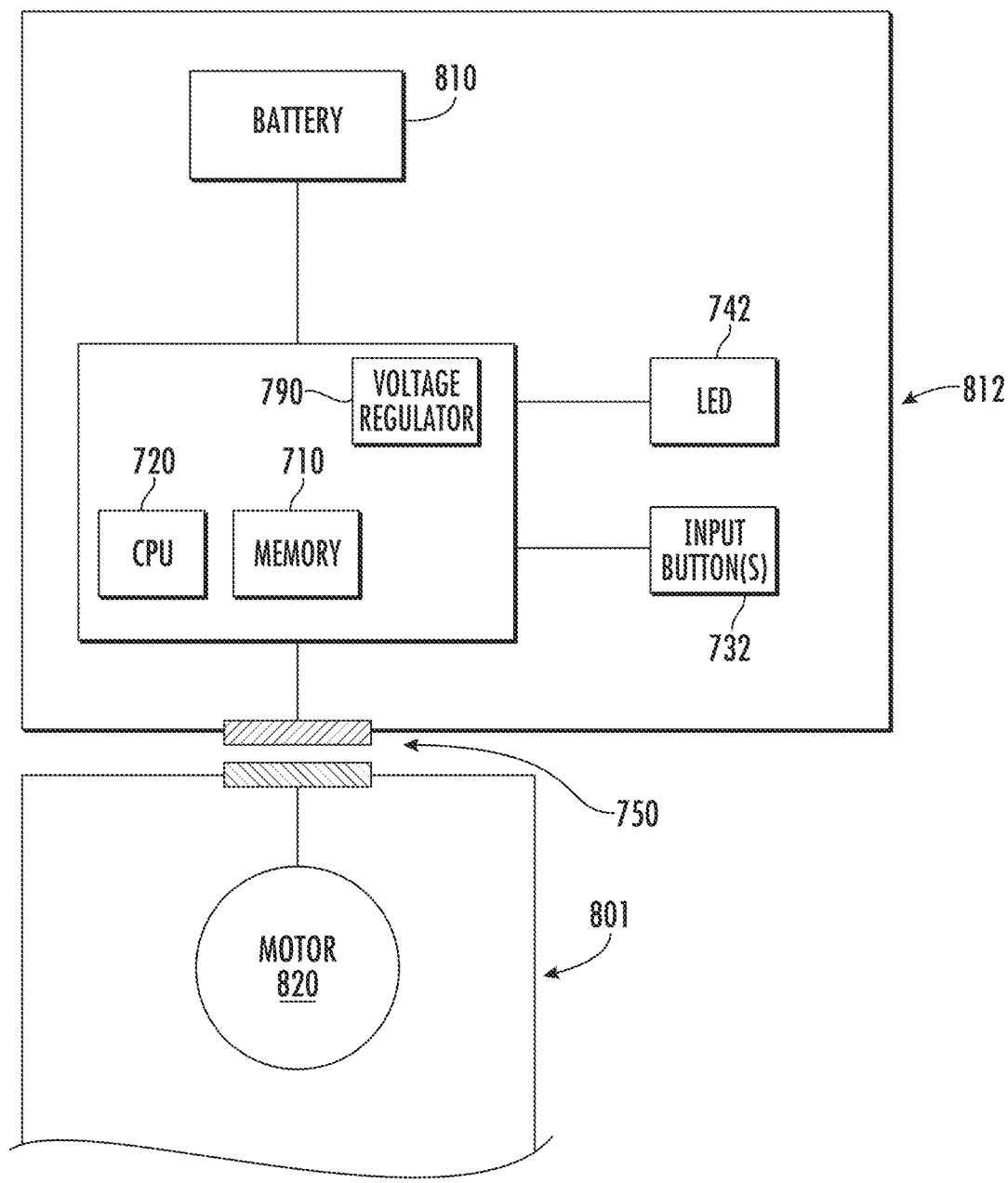
FIG. 12 illustrates a physical configuration of an embodiment of a needling machine control system in which the electronic circuitry is housed together with the battery, and that combined battery-control system is reversibly electronically electable to a needling machine.

FIG. 12 depicts an embodiment of a needle machine control system. Notably, the needle machine control system may be utilized to perform any of the operations of the methods described herein and any of the systems described herein. In certain embodiments, the needle machine control system may include a needling machine 801 and electronic control circuitry 812, which may include a battery 810 as the power source for the needle machine control system, a light emitting diode (LED) 742 to provide visual feedback about the state of the system to a user, one or more input buttons 732 to allow a user to adjust the reference voltage and give level stored in memory 710, a processor 720 that performs various operations for the needle machine control system, a voltage regulator 790 to control voltage provided from battery 810 to motor 820 contained within needling machine 801. In certain embodiments, the processor 720 may compute a baseline current of motor 820, and together with the give level may calculate a threshold current level, which is then stored in memory 710. In certain embodiments, processor 720 may analyze adjustments to be made to the operational voltage stored in voltage regulator 790 based upon the current drawn by the motor 820. In certain embodiments, the electronic control circuitry 812 may be detachably coupled to the needling machine 801 via an electronic connection 750.

In certain embodiments, the battery 810 may be configured to be rechargeable, such as via a cable connected to a port of the electronic control circuitry 812. In certain embodiments, the battery 810 may be recharged via wireless charging as well. and a state of the battery 810 may be indicated via one or more LEDs 742 of the needling machine control system. For example, in certain embodiments, if the battery level of the battery 810 is near depletion, then one or more LEDs 742 may turn red (or any other desired color, sequence of colors, and/or pattern of flashing light). Similarly, if the battery level of the battery 810 is within a threshold range of mid-level power, the one or more LEDs may turn yellow (or any other desired color, sequence of colors, and/or pattern of flashing light). Still further, if the battery level of the battery 810 is within a threshold range of full power, then the one or more LEDs 742 may turn green (or any other desired color, sequence of colors, and/or pattern of flashing light).

In certain embodiments, the one or more LEDs 742 may provide visual feedback about various states of the needling machine control system. For example, as indicated above, the one or more LEDs 742 may provide states relating to the battery level of the battery 810. However, the one or more LEDs 742 may provide other states of the needling machine control system and/or the components of the needling machine control system. For example, the one or more LEDs 742 may provide visual feedback indicating that the processor 720 is performing operations, visual feedback indicating that the memory 710 is storing data and/or instructions for the processor 720, visual feedback associated with adjustments of voltage conducted by the voltage regulator 790, visual feedback associated with activation of one or more of the input buttons 732, visual feedback associated with the operation of the motor 820 (e.g. amount of current drawn by the motor 820, an amount of exertion by the motor 820, whether the motor 820 is overheating, whether the motor 820 is failing, any other information associated with the motor 820, or a combination thereof).

In certain embodiments, as indicated above, the input buttons 732 may be utilized to adjust the reference voltage for the needle machine control system and/or the give level for the needle machine control system. In additional embodiments, the input buttons 732 may also be utilized to adjust how the voltage regulator 790 controls voltage from the battery 810 to the motor 820. For example, the input buttons 732 may be utilized to adjust how rapidly the voltage regulator 790 increases and/or decreases the voltage delivered from the battery 810 to the motor 820 and/or other components of the needle machine control system, when the voltage regulator 790 controls voltage from the battery 810 to the motor 820 and/or other components of the needle machine control system, how often the voltage regulator 790 controls the voltage from the battery 810 to the motor 820 and/or other components of the needle machine control system, under what conditions the voltage regulator 790 control the voltage from the battery 810 to the motor 820 and/or other components of the needle machine control system, and/or specify the current thresholds for triggering operation of the voltage regulator with respect to the various components of the needle machine control system. In further embodiments, the input buttons 732 may also be utilized to control any of the other components of the needle machine control system including, but not limited to, the battery 810, the processor 720, the memory 710, the motor 820, the electronic circuitry 812, the needling machine 801, or a combination thereof.

Figure 13:
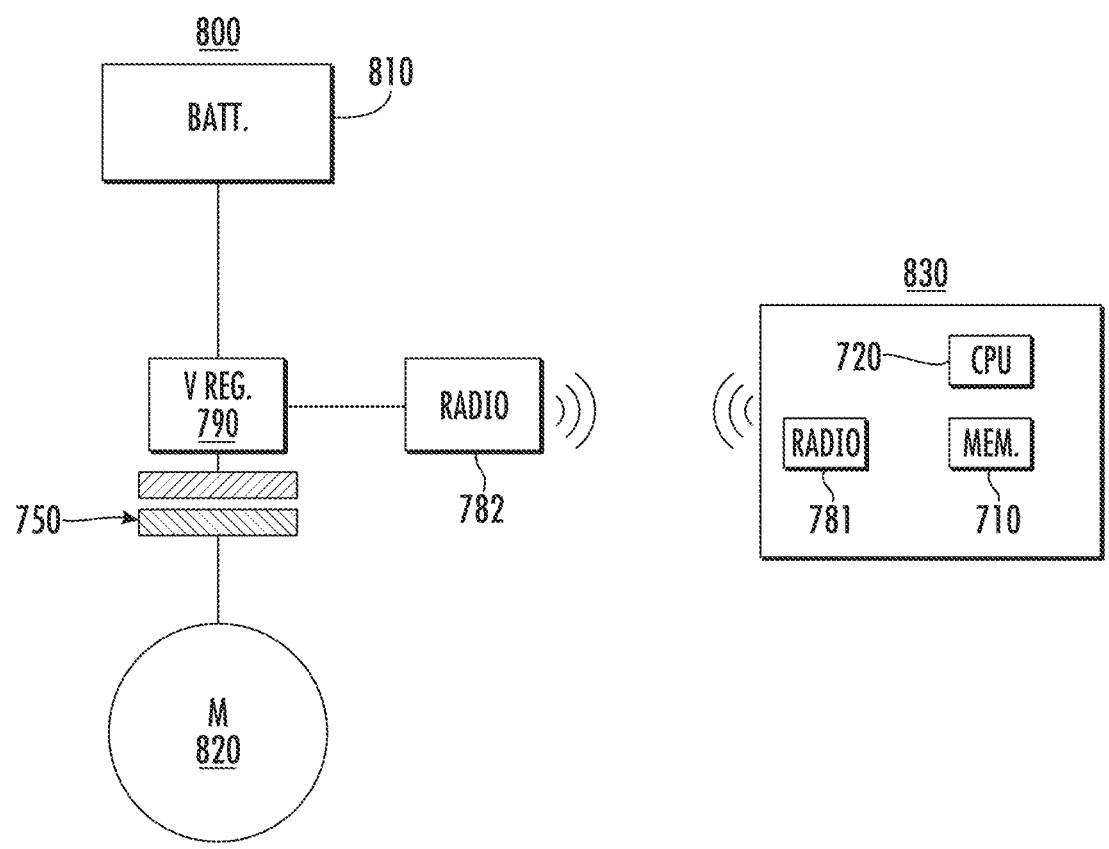
FIG. 13 illustrates another physical configuration of an embodiment of a needling machine control system in which certain components of the system are housed within a wireless control unit, while other components of the system are housed on the wireless needling machine.

An additional embodiment of the present disclosure is illustrated in FIG. 13. In this embodiment, a wireless needling machine 800 may be utilized for the needle machine control system. The wireless needling machine 800 may include a detachable combined battery 810, voltage regulator 790, and first communications device 782, which may be a first radio. An electrical connection 750 allows the electronic components to be removed from needling machine motor 820 and serve as a connection between the motor 820 and the detachable combined battery 810, voltage regulator 790, and/or first radio 782. Dynamic voltage control over needling machine 800 may be achieved by utilizing control unit 830, which may include a second communications device 781 (e.g. a second radio), a processor 720, and a memory 710. Current drawn by motor 820 from battery 810 may be monitored through voltage regulator 790, and the operational current data communicated wirelessly to control unit 830. In turn, control unit 830 may evaluate the observed current, and may determine whether the operational voltage should be increased, decreased, or unchanged via processor 720 evaluating the observed current against a threshold current and reference voltage, which may both be stored in memory 710. An updated operational voltage may then be wirelessly communicated from control unit 830 to voltage regulator 790 via the first and second radios 781 and 782. In certain embodiments, the control unit 830 may be a standalone device, however, in other embodiments, the control unit 830 may reside within or form a part of a smartphone, a smartwatch, a mobile device, a cellular device, a computer, a laptop, a tablet, a phablet, a headset, an IoT device, a media device, any type of device, or a combination thereof.

In certain embodiments, the battery 810 may provide power to the components of the wireless needling machine 800, such as but not limited to, the voltage regulator 790, the radio 782, the motor 820, and/or any other components of the needle machine control system. As with other batteries disclosed in the present disclosure, the battery 810 may be configured to be rechargeable and the needle machine control system may determine and output battery status information to a user of the needle machine control system. In certain embodiments, the voltage regulator 790 may be any type of suitable voltage regulator that may be utilized to monitor current drawn by the motor 820 and/or by other components of the needle machine control system. In certain embodiments, the first and second communications devices 782 and 781 may be any type of communications devices, including, but not limited to, transceivers, cellular antennas, wireless chips, Internet of Things (IoT) devices, wireless modules, communications modules, any other type of communications device, or a combination thereof. In certain embodiments, status information associated with the first communications device 782 may be monitored by the control unit 830. For example, the control unit 830 may determine when the first communications device 782 is transmitting data, when the first communications device 782 is not transmitting data, when the first communications device 782 is ready to receive and/or transmit data, and/or whether the first communications device 782 is communicating with the second communications device 781.

In certain embodiments, in addition to evaluating the observed current associated with the needling machine 800 and determining whether the operational voltage should be increased, decreased, or unchanged, the control unit 830 may perform additional operations with respect to the needling machine 800 and/or other devices of the needling machine control system. In certain embodiments, for example, the control unit 830 may control the operation of the motor 820, provide instructions to the needling machine 800 indicating how much power to deliver to the components of the needling machine 800, adjust how the voltage regulator 790 regulates the delivery of power from the battery 810 to the motor 820 and/or first communications device 782 (and to other components of the needling machine 800), activate or deactivate any of the components of the needling machine 800, monitor each of the components of the needling machine 800, any other operations described in the present disclosure or otherwise, or a combination thereof. In certain embodiments, the control unit 830 may track changes in the voltage and current over time for the needling machine 800, track battery level and other information associated with the battery 810, track the operation of the voltage regulator 790, and track the operations conducted and communications made by the first communications device 782. In certain embodiments, the control unit 830 may compute a baseline current of motor 820 (and/or other components of the needling machine 800), and, utilizing with the selected give level, the control unit 830 may calculate a threshold current level. Each of the calculations and data generated based on the operations of the control unit 830 may be stored in memory 710. In certain embodiments, the processor 720 of the control unit 830 may analyze adjustments to be made to the operational voltage stored in voltage regulator 790 based upon the current drawn by the motor 820. The control unit 830 may also adjust the threshold currents utilized by the needle machine control system as triggers for conducting various operations of the needle machine control system as well.

Figure 14:
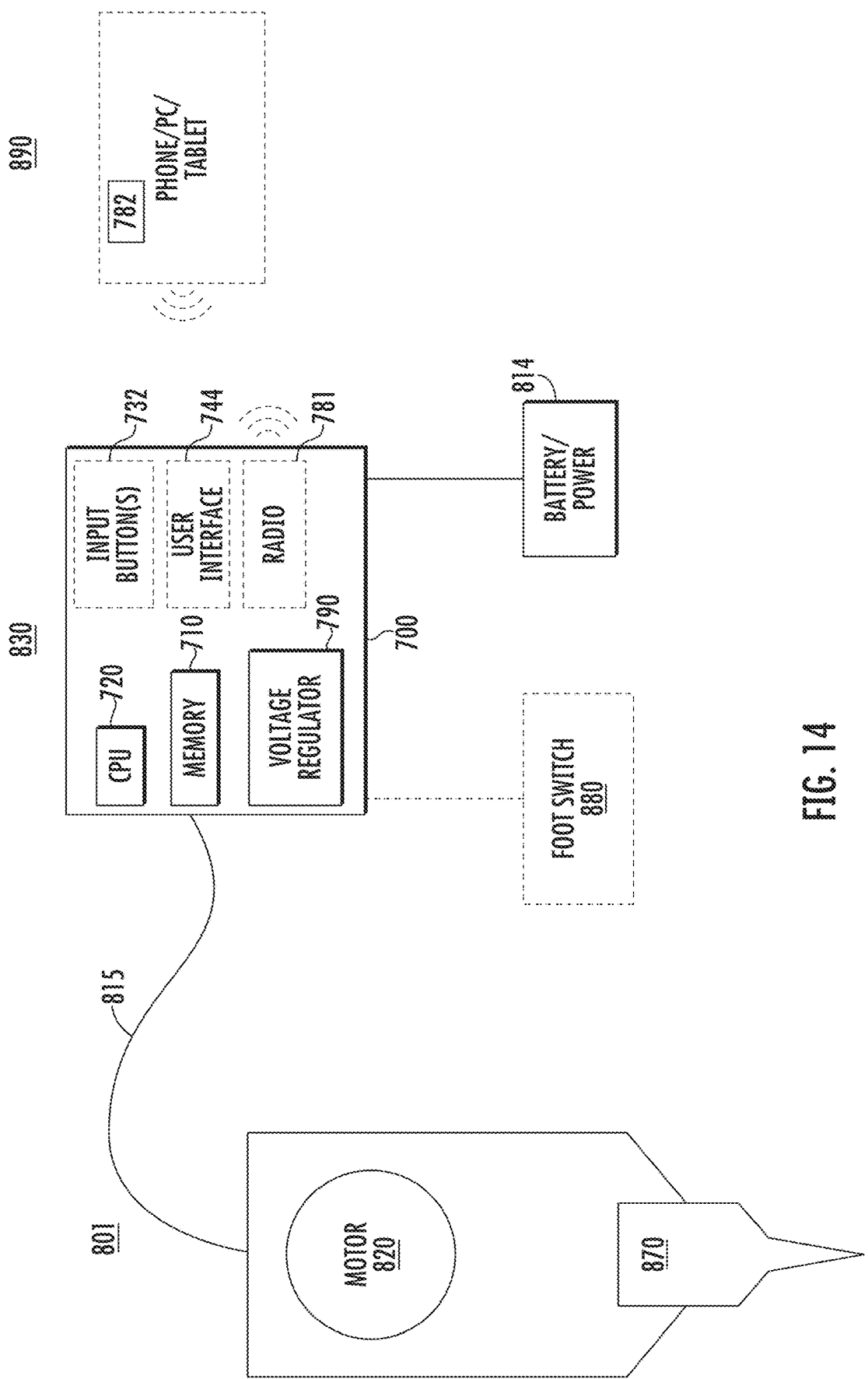
FIG. 14 illustrates yet another physical configuration of an embodiment of a needling machine control system in which the electronic circuitry may be connected wirelessly with peripheral devices from a control unit, while controlling the needling machine by wire.

Still another embodiment of a needle machine control system is depicted in FIG. 14. The needle machine control system may include a needling machine 801, a control unit 830, and/or a peripheral device 890. In certain embodiments, a traditional needling machine 801 may be electrically coupled to and in electrical communication with the control unit 830, such as via wire 815. In certain embodiments, the needling machine 801 may be coupled to an in communication with the control unit 830, such as via a wireless connection. Control unit 830 may be powered from a power source 814, which may include either alternating current (e.g. wall power) or direct current (e.g. battery). Optionally, control unit 830 may include a footswitch 880 for toggling power on and off to the needling machine 801, or for other control functions assignable according to circuitry 700.

Optional input buttons 732 and user interface 744 may be configured to accept a user-defined reference voltage at which needling machine 801 operates under normal conditions (without give adjustment), and a user-defined give level value, both of which may be stored in memory 710. User interface 744 may also continuously provide a user with feedback about the currently-selected give level, reference voltage, operating voltage, along with any other desired information associated with the needle machine control system. Such user feedback may explicitly display the values of the various parameters, or, in certain embodiments, the user interface may provide a simplified means of communicating the status of needling machine 801 and/or control unit 830, such as via color-coded light emitting diodes, and/or even haptic feedback delivered to needling machine 801 through pre-defined sequences of signals sent to motor 820 and/or a haptic device contained within machine 801. In certain embodiments, audible feedback and voice commands may also be provided via the user interface 744. Various combinations of visual, haptic, and/or audible means of communication between the control unit 830, needling machine 801, and/or peripheral device 890 and a user are contemplated by the present disclosure.

Radio 781 may communicatively link to and communicate wirelessly with peripheral device 890. In certain embodiments, the radio 781 may include and/or comprise a transceiver, a communications module, a communications chip, a cellular chip, a radio frequency device, any type of communications device, or a combination thereof. In certain embodiments, peripheral device 890 may consist of a cellular telephone 782, a tablet, a personal computer, a laptop, a smartwatch, an IoT device, a phablet, a robotic device, any type of computing device, or a combination thereof. The radio 781 may be configured to receive data and instructions from the peripheral device 890, which may be utilized to control the needle machine 801, components of the control unit 830, the footswitch 880, the needle cartridge 870, and/or any other components of the needle machine control system. Additionally, data generated by the needle machine 801, the components of the control unit 830, the footswitch 880, the needle cartridge 870, and/or any other components of the needle machine control system may be provided to the peripheral device 890 for further analysis and to facilitate the determining of control instructions for controlling each of the components. The peripheral device 890 may also be utilized to set the conditions at which the needle machine 801 may operate, set the give level, set reference voltages, set operational voltages, set the amount power to be delivered to the components of the needle machine 801, and/or any parameters of the needle machine control system.

In operation, the memory 710 may receive and store the value of the user-selected give level and reference voltage via input 732, and store one or more machine current variables, the final baseline machine current value, and a threshold current value. Voltage regulator 790 may be configured to accept an operational voltage from the electronic circuitry 700, and control the flow of electricity from power source 814 to motor 820 through wire 815. Electronic circuitry 700 may initially assign the reference voltage to the voltage regulator 790, and allow the needling machine 801 to operate for a period of time. During that period of time, electronic circuitry 700 may monitor the current drawn by motor 820, and may establish the baseline machine current variable value and the threshold current value, and store both values in memory 710. In certain embodiments, the peripheral device 890 may perform and/or facilitate any of the operations conducted by the electronic circuitry 700.

As the needle in needle cartridge 870 is applied to a work surface (e.g. such as user's skin) and the needle tip encounters mechanical resistance from the work surface, the motor 820 draws more current from power source 814 via control unit 830 to maintain the machine's operation at the set operational voltage. The control unit 830 monitors the increase in current, and depending on the give level setting, adjusts the operational voltage provided to motor 820 through voltage regulator 790. Electronic circuitry 700 may continuously monitor the current drawn by motor 820, compare that current to the threshold current, compare the operational voltage to the reference voltage, and either increase, decrease, or maintain the operational voltage set in the voltage regulator 790.

Figure 15:
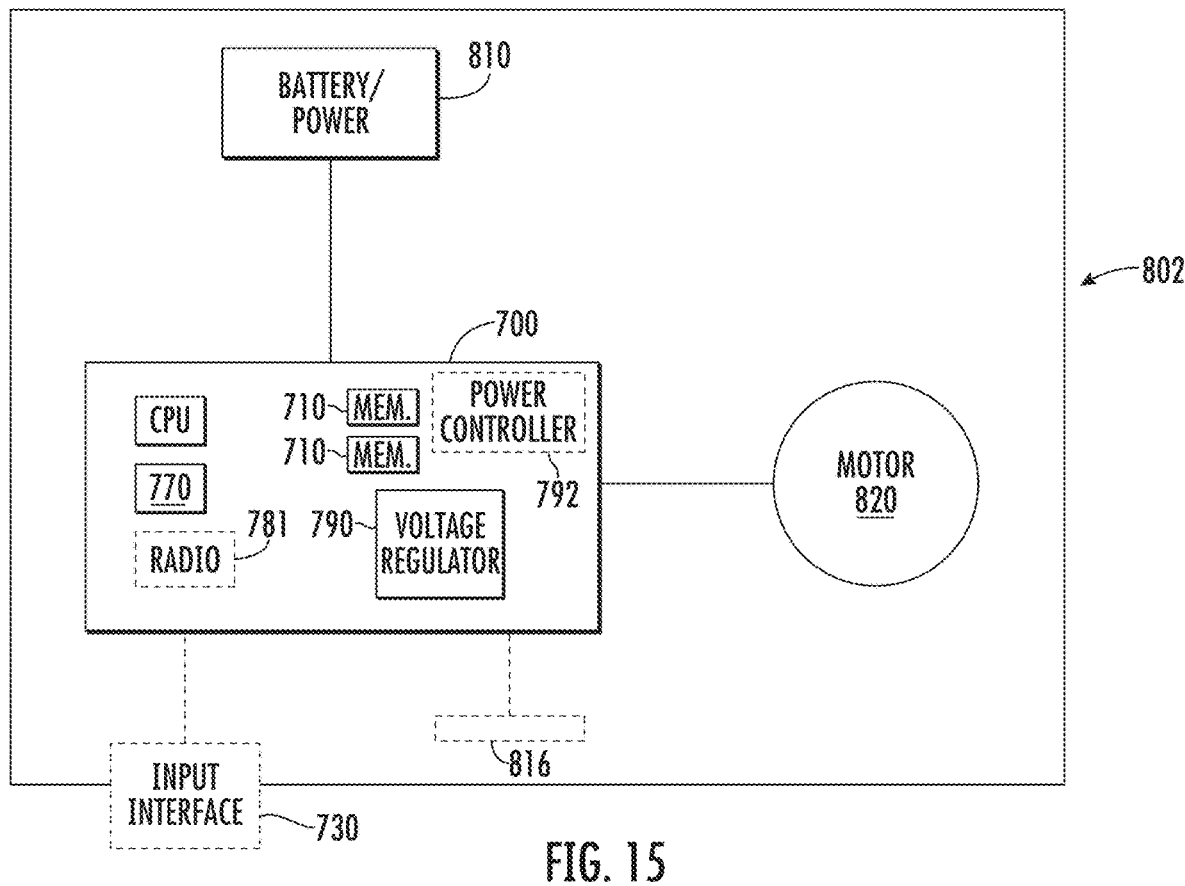
FIG. 15 illustrates still yet a further physical configuration of an embodiment of a needling machine control system in which the entire system is self-contained.

In still yet another embodiment, a needle machine control system is illustrated in FIG. 15, wherein the electronic circuitry 700, battery 810, and motor 820 may be housed within an integrated needling machine 802, and the components are in electrical communication with each other. The needling machine 802 may also include a power controller 792, a voltage regulator 790, one or more memories 710, User input interface 730 and charging port 816 may be provided on an exterior of needling machine 802 and may be in electrical communication with electronic circuitry 700. In certain embodiments, sensor 770 may be provided as part of electronic circuitry 700. The sensor 770 may be configured to monitor the electrical current drawn by motor 820 when the give adjustment circuitry is in operation. In certain embodiments, the sensor 770 may be a single sensor, however, in other embodiments, the sensor 770 may include any number of sensors and/or any types of sensors. For example, the sensor(s) 770 may include pressure sensors, temperature sensors, voltage sensors, current sensors, accelerometers, gyroscopes, light sensors, acoustic sensors, any type of sensors, or a combination thereof. In addition to monitoring the electrical current drawn by the motor 820, the sensor 770 may be configured to monitor a temperature of the components of the needling machine 802, stress experienced by the components of the needling machine 802, the operational voltage within the needling machine 802 at any given time and/or over time, communications occurring within the needling machine 802 and/or between the needling machine 802 and other devices, data stored and/or removed from the memory 710, actions conducted by the power controller 792 and/or voltage regulator 790, inputs coming in via the input interface 730, performance of the motor 820, battery levels of the battery 810 (or other power source), communications made and/or received by the radio 781, movements of the needling machine 802 and/or movements of a needle of a needle cartridge coupled to the needling machine 802, any information associated with the needling machine control system, or a combination thereof.

Figure 16:
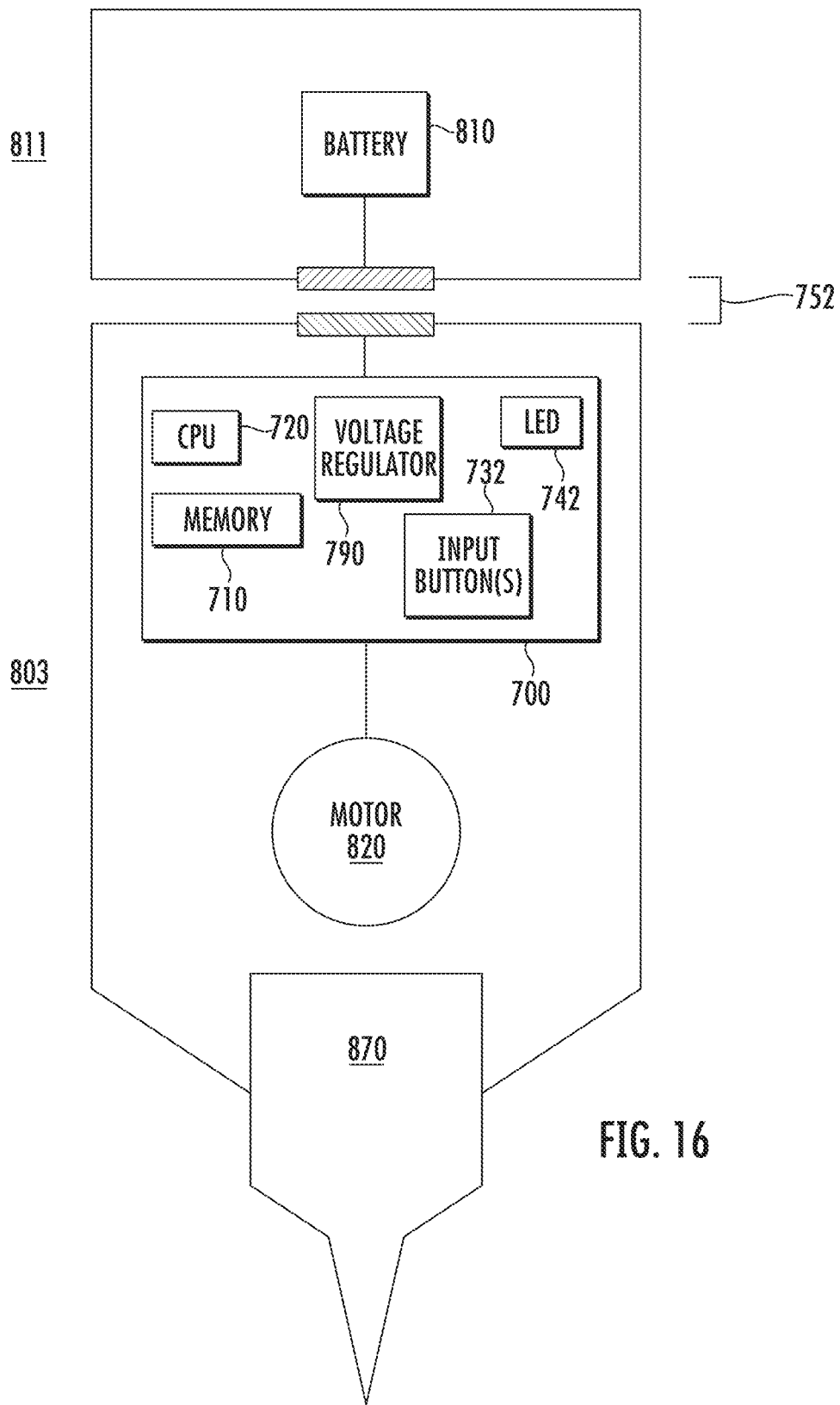
FIG. 16 illustrates another physical configuration of an embodiment of a needling machine control system in which the electronic circuitry is housed within the needling machine, while the power supply is detachable therefrom.

FIG. 16 illustrates a further embodiment of a needle machine control system, wherein the electronic circuitry 700 and motor 820 may be housed within an integrated needling machine 803, and in electrical communication with each other, as well as disconnect able power supply 811, containing battery 810. Power supply 811 and integrated needling machine 803 are disconnectable and may be electrically coupled to each other through interface 752. In certain embodiments, electronic circuitry 700 contains processor 720 in electrical communication with memory 710, voltage regulator 790, input buttons 732, and light emitting diode 742. Voltage regulator 790 may be in electrical communication with power supply 811, and may provide voltage to motor 820. In use, motor 820 may provide mechanical rectilinear actuation of needle cartridge 870 so that a needle of the needle cartridge 870 may perform work on a work surface, such as a user's skin.

Figure 17:
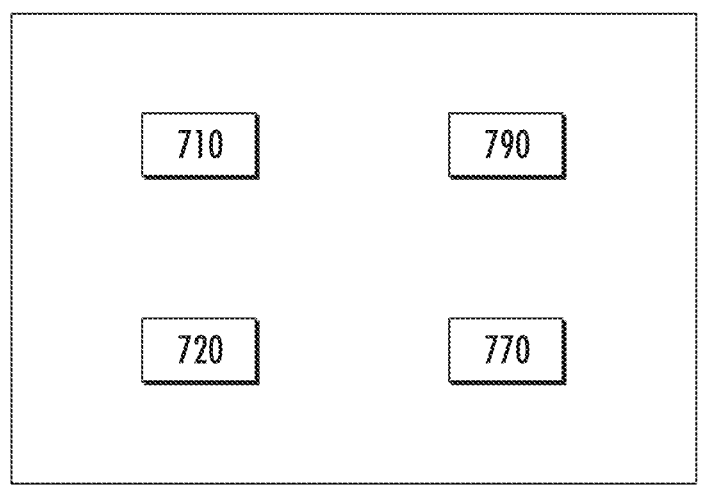
FIG. 17 illustrates the physical configuration of an embodiment of a needling machine control system circuitry.
Figure 18:
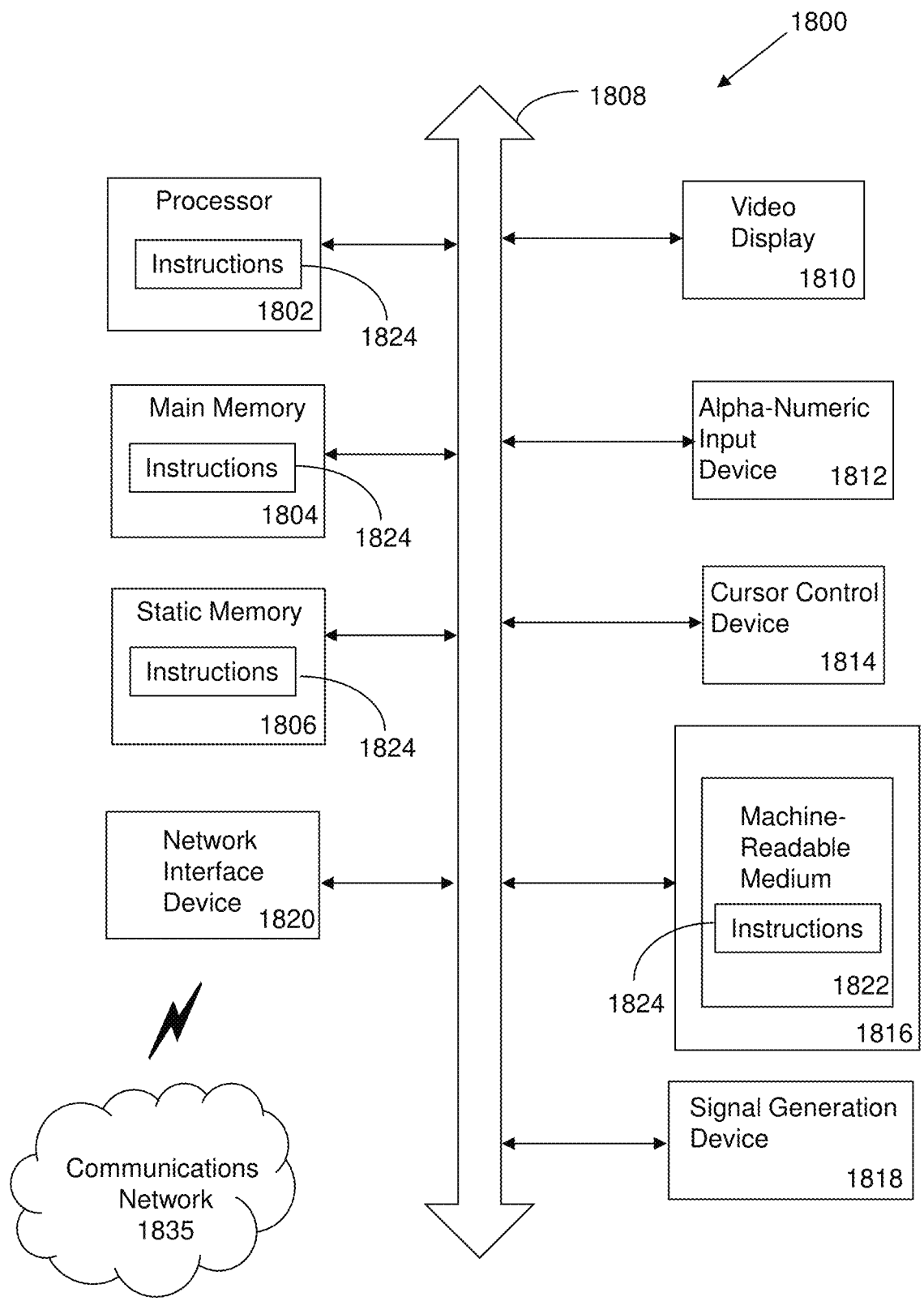
FIG. 18 is a schematic diagram of a machine in the form of a computer system within which a set of instructions, when executed, may cause the machine to perform any one or more of the methodologies or operations of the devices and methods for controlling needle reciprocation.

FIG. 17 illustrates an embodiment of a needling machine control circuit 700. Within the needling machine control circuit 700 may be a memory 710, a processor 720, a current sensor 770, a voltage regulator 790, and/or any other components described in the present disclosure. The needling machine control circuit 700 may store a reference voltage and a give level in the memory 710, both of which may be set by a user, via an input interface linked to the needling machine control circuit 700, and/or by a remote device communicatively linked to the needling machine control circuit 700. In certain embodiments, the memory 710 may also store an absolute lower voltage limit. The needling machine control circuit 700 may sense and continuously monitor the current from sensor 770 when the needling machine control circuit 700 is supplying power from a power source to a needling device coupled to and/or in communication with the needling machine control circuit 700. In certain embodiments, the processor 720 may compute a baseline current and, in turn, compute a threshold current based on the give level, compute an alternative lower voltage limit based on the reference voltage, and compute adjustments to the operational voltage supplied to the voltage regulator 790 based on the observed current and operational voltage, while maintaining the operational voltage between the lower voltage limit and the reference voltage. Notably, the needling machine control circuit 700 may include any of the components and/or functionality described in the present disclosure Referring now also to FIG. 18, at least a portion of the methodologies and techniques described with respect to the exemplary embodiments of the needling machine control systems and/or needling machines can incorporate a machine, such as, but not limited to, computer system 1800, or other computing device within which a set of instructions, when executed, may cause the machine to perform any one or more of the methodologies or functions discussed above. The machine may be configured to facilitate various operations conducted by the needling machine control systems and/or needling machines. For example, the machine may be configured to, but is not limited to, assist the needling machine control systems and/or needling machines by providing processing power to assist with processing loads experienced in the needling machine control systems and/or needling machines, by providing storage capacity for storing instructions or data traversing the needling machine control systems and/or needling machines, or by assisting with any other operations conducted by or within the needling machine control systems and/or needling machines.

In some embodiments, the machine may operate as a standalone device. In some embodiments, the machine may be connected (e.g., using communications network 135, another network, or a combination thereof) to and assist with operations performed by other machines and systems, such as, but not limited to, electronic control circuitry 812, needling machine 801, wireless needling machine 800, control unit 830, peripheral device 890, needling cartridge 870, power source 814, foot switch 880, needling machine 802, power controller 792, voltage regulator 790, processor 720, memory 710, sensors 770, integrated needling machine 803, disconnectable power supply 811, electronic circuitry 700, any other system, program, and/or device, or any combination thereof. The machine may be connected to any one or more components of the needling machine control systems described herein. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 1800 may include a processor 1802 (e.g., a central processing unit (CPU), a graphics processing unit (GPU, or both), a main memory 1804 and a static memory 1806, which communicate with each other via a bus 1808. The computer system 1800 may further include a video display unit 1810, which may be, but is not limited to, a liquid crystal display (LCD), a flat panel, a solid-state display, or a cathode ray tube (CRT). The computer system 1800 may include an input device 1812, such as, but not limited to, a keyboard, a cursor control device 1814, such as, but not limited to, a mouse, a disk drive unit 1816, a signal generation device 1818, such as, but not limited to, a speaker or remote control, and a network interface device 1820.

The disk drive unit 1816 may include a machine-readable medium 1822 on which is stored one or more sets of instructions 1824, such as, but not limited to, software embodying any one or more of the methodologies or functions described herein, including those methods illustrated above. The instructions 1824 may also reside, completely or at least partially, within the main memory 1804, the static memory 1806, or within the processor 1802, or a combination thereof, during execution thereof by the computer system 1800. The main memory 1804 and the processor 1802 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 1822 containing instructions 1824 so that a device (e.g. needling machines) connected to the communications network 1835, another network, or a combination thereof, can send or receive voice, video or data, and communicate over the communications network 1835, another network, or a combination thereof, using the instructions. The instructions 1824 may further be transmitted or received over the communications network 1835, another network, or a combination thereof, via the network interface device 1820.

While the machine-readable medium 1822 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

In light of the foregoing description, it should be recognized that embodiments in accordance with the present disclosure can be realized in numerous configurations contemplated to be within the scope and spirit of the claims. Additionally, the description above is intended by way of example only and is not intended to limit the present disclosure in any way, except as set forth in the claims.

In addition, though the disclosure has been described in reference to several examples optionally incorporating various features, the disclosure is not to be limited to that which is described or indicated as contemplated with respect to each variation of the disclosure. Various changes may be made to the disclosure described and equivalents (whether recited herein or not included for the sake of some brevity) may be substituted without departing from the true spirit and scope of the disclosure. In addition, where a range of values is provided, it is understood that every intervening value, between the upper and lower limit of that range and any other stated or intervening value in that stated range, is encompassed within the disclosure.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present disclosure is not to be limited to the examples provided and/or the subject specification, but rather only by the scope of claim language associated with this disclosure.

What is claimed:

1. A tattoo machine comprising:
a motor;
electronic give adjustment circuitry comprising a voltage regulator in electrical communication with the motor, a processor and a memory, wherein the electronic give adjustment circuitry performs operations comprising:
monitoring a current drawn by the motor, and
setting, based on the current drawn by the motor, an operating voltage provided to the motor from the power source via the voltage regulator, wherein the operating voltage is utilized for setting a reciprocating speed of a needle of the tattoo machine,
receiving a user-selectable give level, and
storing a give range in the memory.

2. The tattoo machine of claim 1, wherein the operations of the electronic give adjustment circuitry further comprise: storing a plurality of machine current readings in the memory, calculating a machine current based upon the plurality of machine current readings, and storing the machine current in the memory.

3. The tattoo machine of claim 2, wherein the operations of the electronic give adjustment circuitry further comprise calculating a threshold current based upon the machine current.

4. The tattoo machine of claim 3, wherein the operations of the electronic give adjustment circuitry further comprise:

hysteretically decrementing the operating voltage supplied to the motor if the current drawn by the motor exceeds the threshold current; and hysteretically incrementing the operating voltage supplied to the motor if the current drawn by the motor is below the threshold current.

5. The tattoo machine of claim 3, wherein the operations of the electronic give adjustment circuitry further comprise adjusting the operating voltage only after receiving at least two consecutive machine current readings above or below the threshold current.

6. The tattoo machine of claim 5, wherein the at least two consecutive machine current readings above the threshold current define a down-voltage state, and the at least two consecutive machine current readings below the threshold current define an up-voltage state, the down-voltage state, the up-voltage state, and a steady-voltage state collectively defining a voltage state.

7. The tattoo machine of claim 2, wherein the operations of the electronic give adjustment circuitry further comprise filtering an irregular current reading drawn by the motor, wherein the filter prevents the electronic circuitry from changing the operating voltage in response to the irregular current reading.

8. The tattoo machine of claim 2, wherein the electronic give adjustment circuitry further includes a ramp-down factor and a ramp-up factor, whereby the operating voltage is decremented by a multiple of the give level and the ramp-down factor and the operating voltage are incremented by a multiple of the give level and the ramp-up factor.

9. The tattoo machine of claim 2, wherein the electronic give adjustment circuitry is further configured so that each hysteretical decrement and each hysteretical increment is defined by the operating voltage minus a product of the give level multiplied, respectively, by a ramp-down factor, or a ramp-up factor, the ramp-down factor and ramp-up factor each having a default value, and the ramp-down factor and the ramp-up factor each increasing upon each consecutive machine current reading above the threshold current, or below the threshold current, respectively.

10. The tattoo machine of claim 9, wherein the operations of the electronic circuitry further comprise resetting the ramp-down factor and the ramp-up factor to the default value upon a change in the voltage state.

11. The tattoo machine of claim 2, wherein the machine current is reestablished upon a triggering event.

12. The tattoo machine of claim 11, wherein the triggering event comprises a change in the reference voltage, turning the tattoo machine on, a power cycling of the tattoo machine, removal of a power source, attachment of a power source, a manual trigger by a user manipulating a user input device, or a combination thereof.

13. The tattoo machine of claim 1, wherein the electronic give adjustment circuitry is further configured to have a lower voltage limit stored in the memory and a reference voltage defining an upper voltage limit.

14. The tattoo machine of claim 1, wherein an external device is configured to monitor the current drawn by the needling machine and control the electrical potential provided to the needling machine from the power source.

* * * * *